US008755492B2

United States Patent
Lee et al.

(10) Patent No.: US 8,755,492 B2
(45) Date of Patent: *Jun. 17, 2014

(54) RADIOGRAPHIC APPARATUS AND CONTROL METHOD THEREOF

(71) Applicant: Samsung Electronics Co., Ltd., Suwon-si (KR)

(72) Inventors: Dong Jae Lee, Hwaseong-si (KR); Soo Sang Yang, Suwon-si (KR); Hyeon Min Lee, Gunpo-si (KR); Jeong Pil Lee, Suwon-si (KR); Woo Sup Han, Yongin-si (KR); Hyun Woong Hwang, Suwon-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 0 days.

This patent is subject to a terminal disclaimer.

(21) Appl. No.: 13/738,221

(22) Filed: Jan. 10, 2013

(65) Prior Publication Data

US 2013/0121477 A1 May 16, 2013

Related U.S. Application Data

(63) Continuation-in-part of application No. 13/237,219, filed on Sep. 20, 2011, now Pat. No. 8,651,740.

(30) Foreign Application Priority Data

Oct. 6, 2010 (KR) .................. 10-2010-0097304

(51) Int. Cl.
*H05G 1/02* (2006.01)
*H05G 1/56* (2006.01)

(52) U.S. Cl.
USPC ........... 378/115; 378/117; 378/196; 378/197; 378/198

(58) Field of Classification Search
USPC .................. 378/115, 117, 196–198
See application file for complete search history.

(56) References Cited

U.S. PATENT DOCUMENTS

| 4,107,590 | A | * | 8/1978 | Pury et al. ...................... 318/628 |
| 4,163,929 | A | * | 8/1979 | Janu et al. ..................... 318/628 |
| 4,674,107 | A | * | 6/1987 | Urban et al. .................... 378/98 |
| 4,697,661 | A | * | 10/1987 | Pajerski et al. ................ 180/6.5 |
| 4,926,455 | A | * | 5/1990 | Stojkov et al. ................ 378/176 |
| 5,351,282 | A | * | 9/1994 | Kadowaki et al. ............ 378/198 |
| 5,416,819 | A | * | 5/1995 | Uzuyama et al. ............. 378/116 |
| 5,768,336 | A | * | 6/1998 | Khutoryansky et al. ...... 378/116 |
| 6,422,747 | B2 | * | 7/2002 | Akutsu et al. ................. 378/198 |

(Continued)

OTHER PUBLICATIONS

Utility U.S. Appl. No. 13/137,634, filed Aug. 30, 2011, Moon, et al., "X-ray Apparatus and Control Method Thereof".*

(Continued)

*Primary Examiner* — Thomas R Artman
(74) *Attorney, Agent, or Firm* — NSIP Law

(57) ABSTRACT

A radiographic apparatus includes an X-ray source unit, a measurement unit configured to measure either one or both of a force and a torque applied to the X-ray source unit, at least one motor configured to move the X-ray source unit, and a system control unit configured to control the at least one motor to move the X-ray source unit according to a direction and a magnitude of the either one or both of the force and the torque measured by the measurement unit.

31 Claims, 14 Drawing Sheets

(56) References Cited

U.S. PATENT DOCUMENTS

| | | | |
|---|---|---|---|
| 6,851,851 B2* | 2/2005 | Smith et al. | 378/189 |
| 6,871,715 B1* | 3/2005 | Diaz Carmena et al. | 180/65.51 |
| 7,177,393 B2* | 2/2007 | Kanemitsu | 378/117 |
| 7,534,037 B2* | 5/2009 | Curtis | 378/197 |
| 7,597,473 B2* | 10/2009 | Graumann et al. | 378/197 |
| 8,201,999 B2* | 6/2012 | Uchida et al. | 378/197 |
| 2009/0285355 A1* | 11/2009 | Brada et al. | 378/20 |
| 2010/0243924 A1* | 9/2010 | Uchida et al. | 250/522.1 |
| 2012/0087479 A1* | 4/2012 | Moon et al. | 378/189 |
| 2012/0087480 A1* | 4/2012 | Yang et al. | 378/197 |
| 2012/0155616 A1* | 6/2012 | Rijken et al. | 378/198 |

OTHER PUBLICATIONS

Utility U.S. Appl. No. 13/237,219, filed Sep. 20, 2011, Yang, et al., "Radiography System and Moving Method Thereof".*

Korean Office Action issued on Jun. 24, 2013, in counterpart Korean Application No. 10-2010-0097304 (16 pages, including complete English translation translated by Google Translate).

* cited by examiner

RADIOGRAPHIC APPARATUS AND CONTROL METHOD THEREOF

CROSS-REFERENCE TO RELATED APPLICATIONS

This application is a continuation-in-part of application Ser. No. 13/237,219 filed on Sep. 20, 2011, now U.S. Pat. No. 8,651,740 issued on Feb. 18, 2014, and claims the benefit of Korean Patent Application No. 10-2010-0097304 filed on Oct. 6, 2010, in the Korean Intellectual Property Office, the disclosures of which are incorporated herein by reference in their entirety for all purposes.

BACKGROUND

1. Field

This application relates to a radiographic apparatus that can be moved by an operator using a reduced force and a control method thereof.

2. Description of Related Art

A radiographic apparatus is designed to obtain an internal image of a human body using X-rays. The radiographic apparatus is used to inspect injuries of an internal part or diseases of the human body that are not easily checked by the external appearance of the human body.

The radiographic apparatus obtains an internal image of the human body by radiating X-rays to a desired region to be photographed (imaged), such as a head part and a chest part of the human body, and by detecting X-rays transmitted through the region.

The radiographic apparatus is provided with an X-ray tube to radiate X-rays to a desired region. The X-ray tube is mounted to be movable to inspect various regions of the human body.

In general, a ceiling type radiographic apparatus is provided with at least one guide rail installed on the ceiling of an inspection room, and a telescoping post frame mounted on the guide rail. The X-ray tube is rotatably installed on a lower end of the telescoping post frame.

In recent years, the ceiling type radiographic apparatus has been provided with an automatic movement mode by installing an actuator on an axis of movement of the ceiling type radiographic apparatus, and as an operator inputs a desired position, the X-ray tube automatically moves to the position input by the operator.

In addition, the radiographic apparatus may have a manual movement mode for the operator to manually move the X-ray tube. A manual operating switch is provided near the X-ray tube, and the operator may manually move the X-ray tube after switching the operation mode from the automatic movement mode to the manual movement mode using the manual operating switch.

Due to the weight of the X-ray tube and the frictional resistance of the moving parts of the radiographic apparatus, the operator needs to apply a large force or torque to the X-ray tube to move the X-ray tube in the manual movement mode. Accordingly, when there is a need for a repetitive movement of the X-ray tube, the operator may experience physical fatigue.

SUMMARY

In one general aspect, a radiographic apparatus includes an X-ray source unit; a measurement unit configured to measure either one or both of a force and a torque applied to the X-ray source unit; at least one motor configured to move the X-ray source unit; and a system control unit configured to control the at least one motor to move the X-ray source unit according to a direction and a magnitude of the either one or both of the force and the torque measured by the measurement unit.

The measurement unit may include a sensor configured to measure forces in directions of three axes intersecting one another, or to measure at least one torque having at least one of the three axes as a rotation axis, or to measure the forces in the directions of the three axes intersecting one another and the at least one torque having the at least one of the three axes as a rotation axis.

The radiographic apparatus may further include a manipulating unit mounted on the measurement, unit; and the measurement unit may be mounted on the X-ray source unit so that the measurement unit may be between the manipulating unit and the X-ray source unit.

The manipulating unit may include a display unit configured to provide an interface for manipulation of the radiographic apparatus; and a grip configured to apply the either one or both of the force and the torque to the X-ray source unit.

The system control unit may be further configured to generate a control signal corresponding to the direction and the magnitude of the either one or both of the force and the torque, and output the generated control signal to the at least one motor to operate the at least one motor in a driving direction and with a driving force that respectively correspond to the direction and the magnitude of the either one or both of the force and the torque.

The at least one motor may include a plurality of motors; and the system control unit may be further configured to determine which motor of the plurality of motors corresponds to the direction of the either one or both of the force and the torque, and determine a driving speed of the determined motor based on the magnitude of the either one or both of the force and the torque.

The system control unit may be further configured to calculate a difference between the determined driving speed and an actual moving speed of the X-ray source unit, and reduce the moving speed of the X-ray source unit or stop moving the X-ray source unit if the difference exceeds a predetermined difference.

The system control unit may be further configured to remove a signal having a frequency range corresponding to a resonance frequency range of the radiographic apparatus from the control signal to reduce a vibration generated when the X-ray source unit moves.

The radiographic apparatus may further includes a first guide rail mounted on a ceiling and extending in a first direction; the X-ray source unit may be configured to move in the first direction along the first guide rail; and the at least one motor may include a first motor configured to move the X-ray source unit in the first direction.

The radiographic apparatus may further include a second guide rail slidably mounted on the first rail and extending in a second direction perpendicular to the first direction; the X-ray source unit may be further configured to move in the second direction along the second guide rail; and the at least one motor may further include a second motor configured to move the X-ray source unit in the second direction.

The radiographic apparatus may further include a post frame configured to have a length that is increasable and decreasable in a third direction perpendicular to the first direction and the second direction; the X-ray source unit may be further configured to move in the third direction according to an increase and a decrease of the length of the post frame;

and the at least one motor may further include a third motor configured to move the X-ray source unit in the third direction.

The radiographic apparatus may further include a first rotating joint configured to rotate in a fourth direction about an axis parallel to the third direction; the X-ray source unit may be connected to the first rotating joint to enable the X-ray source unit to rotate in the fourth direction; and the at least one motor may further include a fourth motor configured to rotate the X-ray source unit in the fourth direction.

The radiographic apparatus may further include a second rotating joint configured to rotate in a fifth direction about an axis parallel to the first direction; the X-ray source unit may be connected to the second rotating joint to enable the X-ray source unit to rotate in the fifth direction; and the at least one motor may further include a fifth motor configured to rotate the X-ray source unit in the fifth direction.

The radiographic apparatus may further include a link board configured to receive signals measured by the measurement unit, and transmit the received signals; a cable connected to the link board and the system control unit to transmit the transmitted signals from the link board to the system control unit; and a motor driver configured to operate the at least one motor according to the control signal generated by the system control unit.

The measurement unit may include a force/torque sensor configured to measure forces in directions of three axes intersecting one another, or to measure at least one torque having at least one of the three axes as a rotation axis, or to measure the forces in the directions of the three axes intersecting one another and the at least one torque having the at least one of the three axes as a rotation axis.

The radiographic apparatus may further include a collision sensor configured to sense an object in a moving direction of the X-ray source unit and output a signal corresponding to a distance to the sensed object; and the system control unit may be further configured to control the at least one motor to prevent the X-ray source unit from colliding with the object based on the signal output from the collision sensor.

In another general aspect, a radiographic apparatus includes an X-ray source unit; a measurement unit configured to measure either one or both of a force and a torque applied to the X-ray source unit; and a control unit configured to control movement of the X-ray source unit based on the either one or both of the force and the torque measured by the measurement unit.

The radiographic apparatus may further include at least one motor configured to move the X-ray source unit under control of the control unit.

The control unit may be further configured to control the movement of the X-ray source unit according to a direction and a magnitude of the either one or both of the force and the torque measured by the measurement unit.

The measurement unit may include a sensor configured to measure forces in directions of three axes intersecting one another, or to measure at least one torque having at least one of the three axes as a rotation axis, or to measure the forces in the directions of the three axes intersecting one another and the at least one torque having the at least one of the three axes as a rotation axis.

The radiographic apparatus may further include a manipulating unit configured to be manipulated by an operator to apply the either one or both of the force and the torque to the X-ray source unit.

The radiographic apparatus may further include a collision sensor configured to sense an object in a moving direction of the X-ray source unit and output a signal corresponding to a distance to the sensed object; and the control unit may be further configured to control the movement of the X-ray source unit to prevent the X-ray source unit from colliding with the object based on the signal output from the collision sensor.

In another general aspect, a radiographic apparatus includes an X-ray source unit; a manipulating unit configured to provide an interface for manipulation of the radiographic apparatus, the manipulating unit including a display unit configured to display information related to an X-ray imaging operation; a sensor unit configured to sense an X-axis force and a Y-axis force applied to the manipulating unit; a first motor configured to move the X-ray source unit in a D1 direction; a second motor configured to move the X-ray source unit in a D2 direction; and a system control unit configured to control the first motor to move the X-ray source unit in the D1 direction based on the X-axis force sensed by the sensor unit, and control the second motor to move the X-ray source unit in the D2 direction based on the Y-axis force sensed by the sensor unit.

The manipulating unit may includes a grip adapted to be manipulated by a single hand of an operator to control movement of the X-ray source unit.

The system control unit may be further configured to control both the first motor and the second motor simultaneously to move the X-ray source unit in both the D1 direction and the D2 direction simultaneously if both the X-axis force and the Y-axis force are sensed simultaneously by the sensor unit.

No clutch may be provided to disengage the first motor from the X-ray source unit, and no clutch may be provided to disengage the second motor from the X-ray source unit; and no brake may be provided to stop movement of the X-ray source unit in the D1 direction, and no brake may be provided to stop movement of the X-ray source unit in the D2 direction.

The radiographic apparatus may further include a third motor configured to move the X-ray source unit in a D3 direction; the sensor unit may be further configured to sense a Z-axis force applied to the manipulating unit; and the system control unit may be further configured to control the third motor to move the X-ray source unit in the D3 direction based on the Z-axis force sensed by the sensor unit.

No clutch may be provided to disengage the first motor from the X-ray source unit, no clutch may be provided to disengage the second motor from the X-ray source unit, and no clutch may be provided to disengage the third motor from the X-ray source unit; and no brake may be provided to stop movement of the X-ray source unit in the D1 direction, no brake may be provided to stop movement of the X-ray source unit in the D2 direction, and no brake may be provided to stop movement of the X-ray source unit in the D3 direction.

The radiographic apparatus may further include a collision sensor configured to sense an object in a moving direction of the X-ray source unit and output a signal corresponding to a distance to the sensed object; and the system control unit may be further configured to control either one or both of the first motor and the second motor to prevent the X-ray source unit from colliding with the object based on the signal output from the collision sensor.

Other features and aspects will be apparent from the following detailed description, the drawings, and the claims.

DETAILED DESCRIPTION

Figure 1:
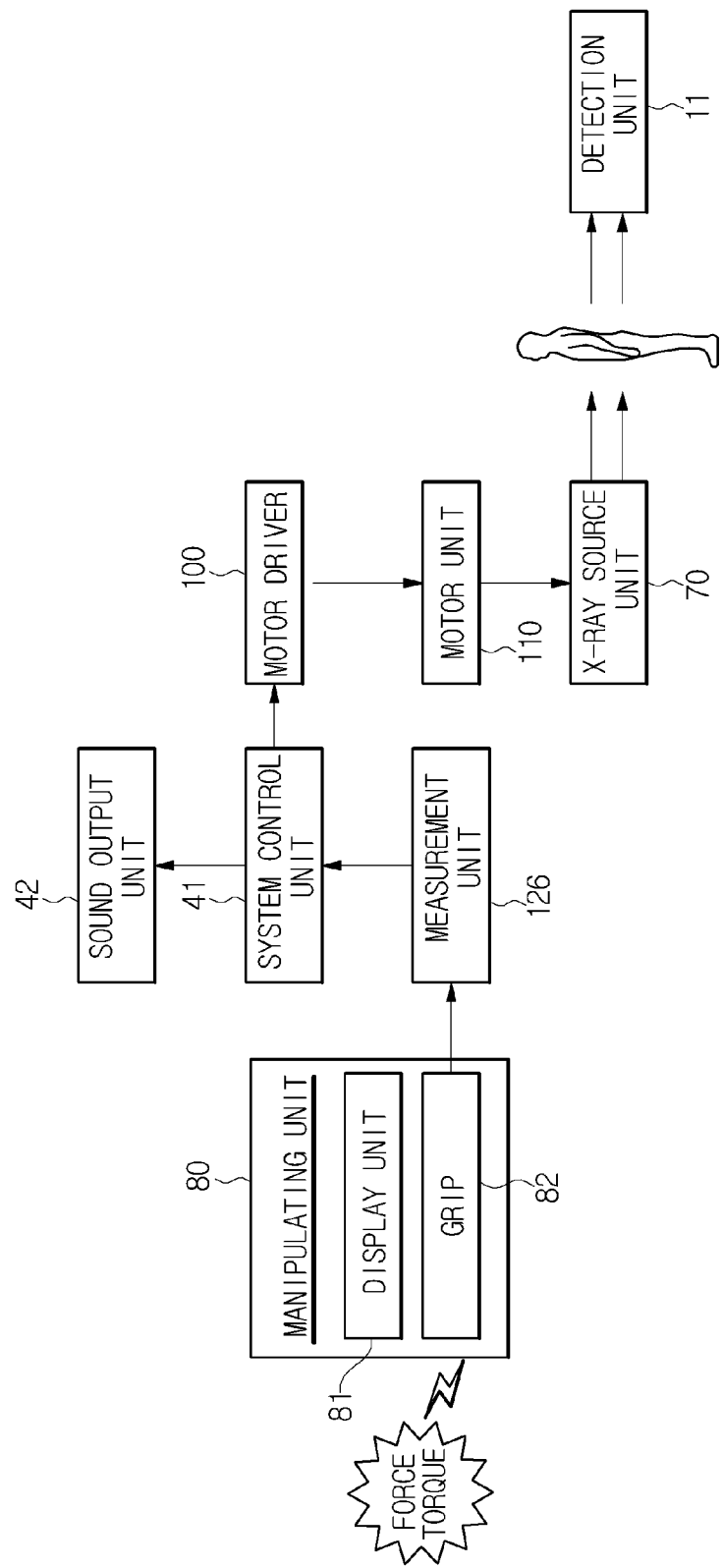
FIG. 1 is a block diagram illustrating the configuration of a radiographic apparatus in accordance with one example.

The following detailed description is provided to assist the reader in gaining a comprehensive understanding of the methods, apparatuses, and/or systems described herein. However, various changes, modifications, and equivalents of the methods, apparatuses, and/or systems described herein will be apparent to one of ordinary skill in the art. Also, descriptions of functions and constructions that are well known to one of ordinary skill in the art may be omitted for increased clarity and conciseness.

Throughout the drawings and the detailed description, the same reference numerals refer to the same elements. The drawings may not be to scale, and the relative size, proportions, and depiction of elements in the drawings may be exaggerated for clarity, illustration, and convenience.

Figure 2:
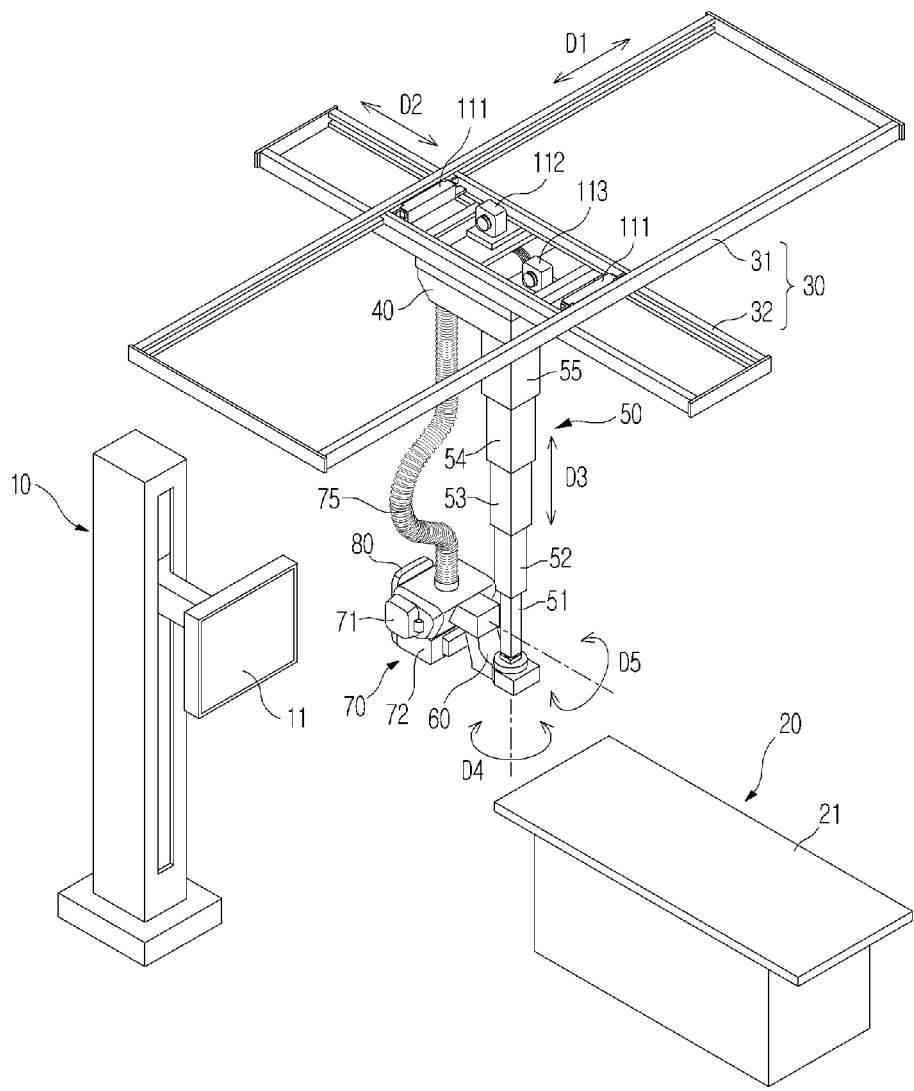
FIG. 2 is a perspective view illustrating the configuration of the radiographic apparatus of FIG. 1 in accordance with example.
Figure 3:
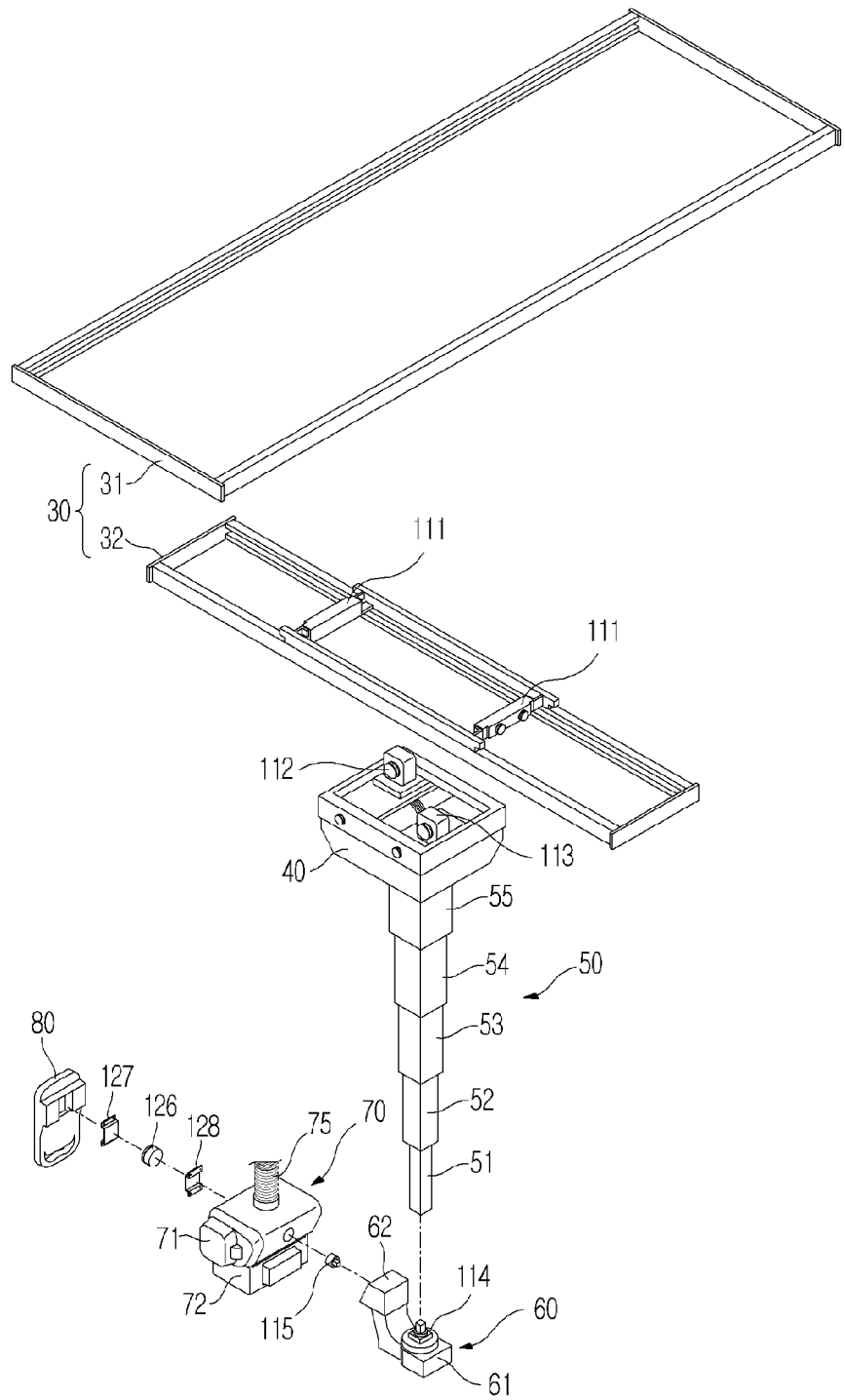
FIG. 3 is an exploded perspective view illustrating the configuration of a portion of the radiographic apparatus of FIGS. 1 and 2 in accordance with one example.
Figure 4:
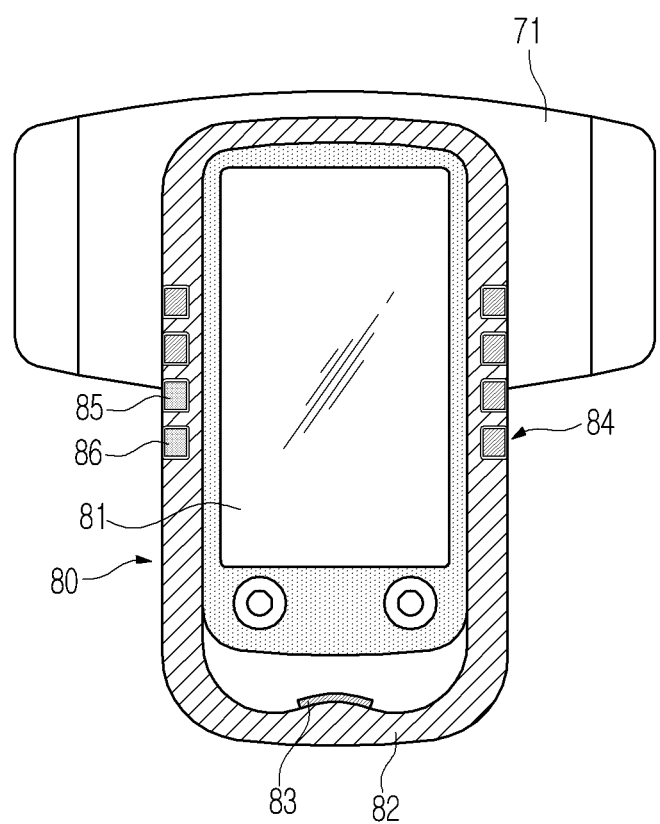
FIG. 4 is a front view illustrating a manipulating unit of the radiographic apparatus of FIGS. 1-3 in accordance with one example.
Figure 10:
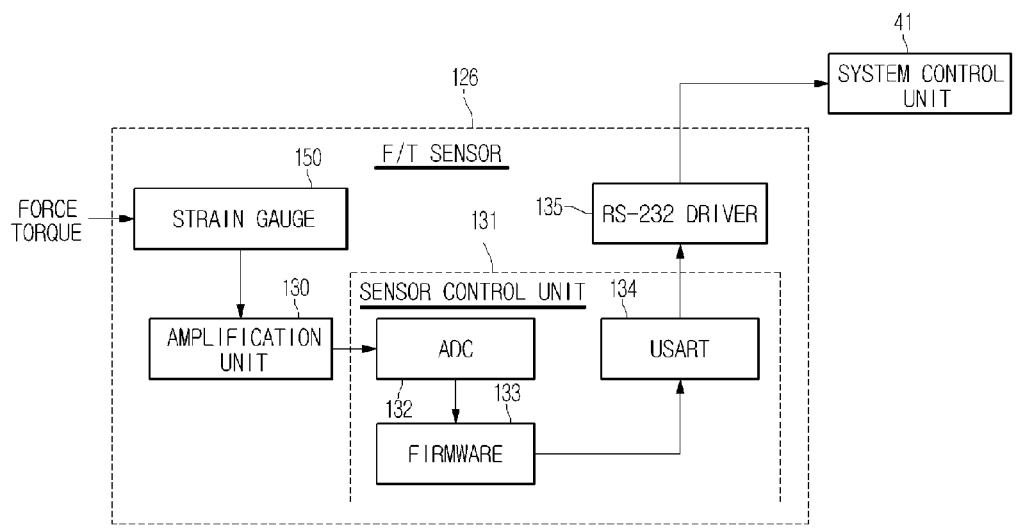
FIG. 10 is a block diagram illustrating the force/torque sensor of FIGS. 5-9 in accordance with one example.
Figure 11:
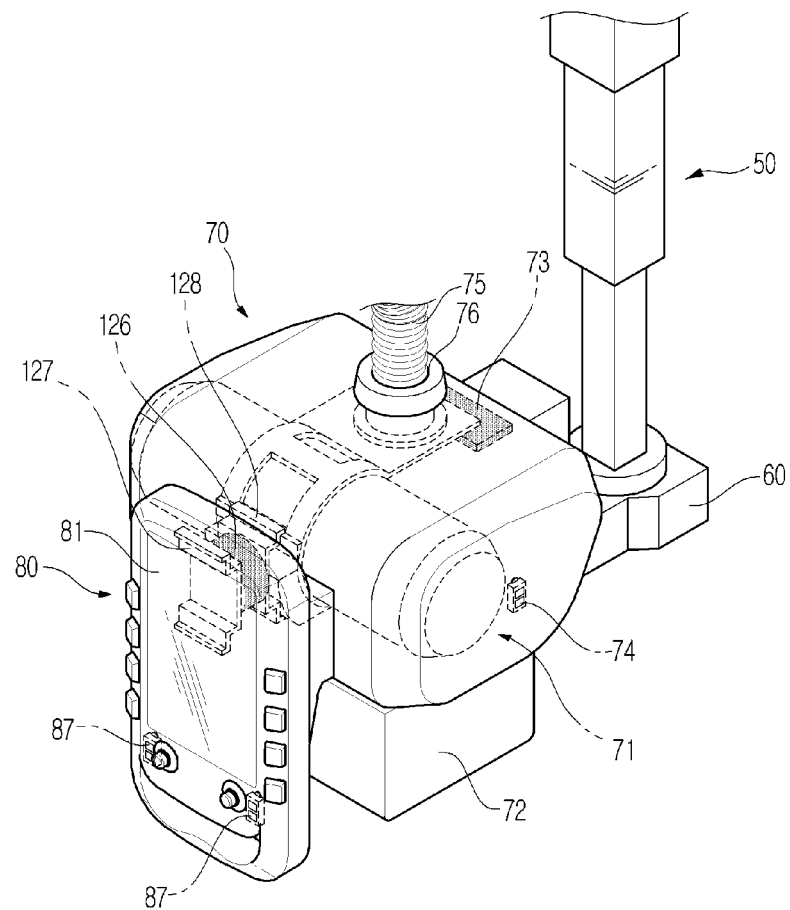
FIG. 11 is a perspective view illustrating the internal structure of the manipulating unit, a measurement unit, and a photographic unit of the radiographic apparatus of FIGS. 1-10 in accordance with one example.
Figure 12:
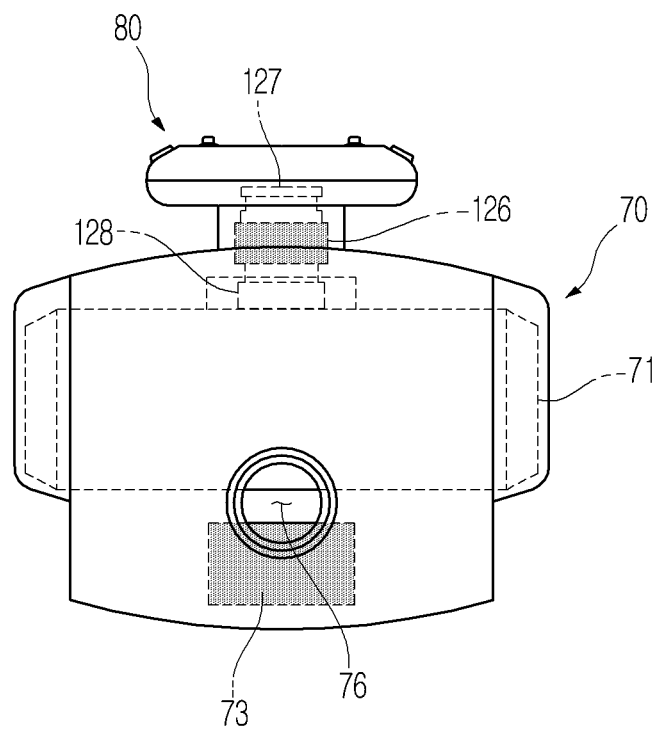
FIG. 12 is a top view illustrating the manipulating unit, the measurement unit, and the photographic unit of FIG. 11 in accordance with one example.

FIG. 1 is a block diagram illustrating the configuration of a radiographic apparatus in accordance with one example. FIG. 2 is a perspective view illustrating the configuration of the radiographic apparatus of FIG. 1 in accordance with one example. FIG. 3 is an exploded perspective view illustrating the configuration of a portion of the radiographic apparatus of FIGS. 1 and 2 in accordance with one example. FIG. 4 is a front view illustrating a manipulating unit of the radiographic apparatus of FIGS. 1-3 in accordance with one example. FIG. 11 is a perspective view illustrating the internal structure of the manipulating unit, a measurement unit, and a photographic unit of the radiographic apparatus of FIGS. 1-10 in accordance with one example. FIG. 12 is a top view illustrating the manipulating unit, the measurement unit, and the photographic unit of FIG. 11 in accordance with one example.

Referring to FIG. 1, a radiographic apparatus includes a manipulating unit 80 that is configured to provide an interface for manipulation of the radiographic apparatus, and includes a display unit 81 configured to provide an interface through which information related to X-ray imaging is input and each part of the radiographic apparatus is manipulated, and a grip 82 configured to be gripped by an operator to manually manipulate the radiographic apparatus, a measurement unit 126 (sensor unit) configured to measure (to sense) a force or a torque applied to the photographic unit 70 through the grip 82 of the manipulating unit 80, a system control unit 41 configured to generate a control signal to move a photographic unit 70 (X-ray source unit) based on a measurement result of the measurement unit 126, a motor driver 100 configured to drive a motor unit 110 according to the control signal of the system control unit 41, the motor unit 110 being configured to apply a driving force to move the photographic unit 70, the photographic unit 70 being configured to photograph an object, such as a patient, by radiating X-rays to the object, and a detection unit 11 (X-ray detection unit) configured to detect X-rays transmitted through the object. The system control unit 41 outputs an alarm sound indicating movement of the photographic unit 70 through a sound output unit 42, thereby notifying the operator that the movement of the photographic unit 70 is being performed with the assistance of the motor unit 110. Each part of the radiographic apparatus will be described in detail below with reference to FIGS. 2 to 4.

Referring to FIGS. 2 and 3, the radiographic apparatus includes a guide rail unit 30, a moving carriage 40 inside which the system control 41 is mounted, a telescoping post frame 50 (hereinafter referred to as simply the post frame 50), the motor unit 110, the photographic unit 70, the measurement unit 126, and the manipulating unit 80.

The radiographic apparatus further includes a photographic stand 10 supporting the detection unit 11 configured to detect the X-rays transmitted through the object, and a photographic table 20 including a surface 21 configured to support an object to be photographed, such as a patient.

The guide rail unit 30, the moving carriage 40, and the post frame 50 enable the photographic unit 70 to be moved toward the object.

The guide rail unit 30 includes a first guide rail 31 and a second guide rail mounted at a predetermined angle with respect to each other. In the example of FIGS. 2 and 3, the first guide rail 31 extends in a direction perpendicular to a direction in which the second guide rail 32 extends.

The first guide rail 31 is mounted on a ceiling of an inspection room in which the radiographic apparatus is installed.

The second guide rail 32 is disposed below the first guide rail 31, and is slidably mounted on the first guide rail 31. The second guide rail 32 is includes rollers (not shown) that are movable along the first guide rail 31.

The direction in which the first guide rail 31 extends is defined as a first direction D1, and the direction in which the second guide rail 32 extends is defined as a second direction D2. Accordingly, the first direction D1 and the second direction D2 are perpendicular to each other and are parallel to the ceiling of the inspection room.

The moving carriage 40 is disposed below the second guide rail 32, and is slidably mounted on the second guide rail 32.

The moving carriage 40 includes rollers (not shown) that are movable along the second guide rail 32.

Accordingly, the moving carriage 40 is movable in the first direction D1 together with the second guide rail 32, and is also movable in the second direction D2 along the second guide rail 32. The system control unit 41 is mounted inside the moving carriage 40, and is configured to generate a control signal based on the measurement result of the measurement unit 126, and transmit the generated control signal to the motor driver 100.

The post frame 50 is disposed below the moving carriage 40 and is mounted on the moving carriage 40. The post frame 50 includes a plurality of posts 51, 52, 53, 54, and 55.

The plurality of posts 51, 52, 53, 54, and 55 form a telescoping structure that enables the length of the post frame 50 to be increased or decreased in a vertical direction in the inspection room while mounted on the moving carriage 40.

The direction in which the length of the post frame 50 increase or decreases is defined as a third direction D3. Accordingly, the third direction D3 is perpendicular to the first direction D1 and the second direction D2.

The photographic unit 70 is an apparatus configured to radiate X-rays to an object. The photographic unit 70 includes an X-ray tube 71 to generate X-rays, and a collimator 72 to guide the generated X-rays to the object. The photographic unit 70 may also be provided with a collision sensor 74 (not shown in FIGS. 1-3, but shown in FIG. 11). The illustration in FIG. 11 is merely an example of the collision sensor 74, and the position of the collision sensor 74 is not limited to the position shown in FIG. 11. Also, additional collision sensors 74 may be provided at other locations on the photographic unit 70, such as on the other side of the photographic unit 70 from the collision sensor 74 shown in FIG. 11, or on the other side of the photographic unit 70 from the manipulating unit 80. In one example, the collision sensor 74 is an optical sensor configured to sense an object in a moving direction of the photographic unit 70 and output a signal corresponding to a distance to the sensed object. The system control unit 41 is configured to control the motors 111, 112, and 113 to prevent the photographic unit 70 from colliding with the sensed object based on the signal output from the collision sensor 74.

A rotating joint unit 60 is disposed between the photographic unit 70 and the post frame 50. The rotating joint unit 60 couples the photographic unit 70 to the post frame 50 while supporting the load acting on the photographic unit 70.

The rotating joint unit 60 includes a first rotating joint 61 connected to a bottom post 51 of the post frame 50, and a second rotating joint 62 connected to the photographic unit 70.

The first rotating joint 61 is configured to be rotatable about a central axis of the post frame 50 that extends in the vertical direction in the inspection room. Accordingly, the first rotating joint 61 is rotatable in a plane that is perpendicular to the third direction D3. The rotating direction of the first rotating joint 61 is defined as a fourth direction D4, that is, a direction of rotation about an axis parallel to the third direction D3.

The second rotating joint 62 is configured to be rotatable in a plane that is perpendicular to the ceiling of the inspection room. Accordingly, the second rotating joint 62 is rotatable in a direction of rotation about an axis that may be parallel to the first direction D1 or the second direction D2, depending on a rotation of the first rotating joint 61 in the fourth direction D4. The rotating direction of the second rotating joint 62 is defined as a fifth direction D5, that is a direction of rotation about an axis that may extend parallel to the first direction D1 or the second direction D2, depending on a rotation of the first rotating joint 61 in the fourth direction D4.

Accordingly, the photographic unit 70 is rotatable in the fourth direction D4 and the fifth direction D5 while connected to the rotating joint unit 60, and is also movable in the first direction D1, the second direction D2, and the third direction D3 while connected to the post frame 50 through the rotating joint unit 60.

In order to move the photographic unit 70 in the first direction D1 to the fifth direction D5, the motor unit 110 is provided. The motor unit 110 may include a plurality of motors, each of which may be an electrical motor, and may include an encoder configured to provide information on the speed and position of a shaft of the motor.

The motor unit 110 may be provided with a first motor 111, a second motor 112, a third motor 113, a fourth motor 114, and a fifth motor 115 respectively corresponding to the first to fifth directions D1 to D5. In the example in FIGS. 2 and 3, two motors 111 are provided.

For the convenience of design, the motors 111, 112, 113, 114 and, 115 may be disposed at various positions. For example, the first motors 111 configured to move the second guide rail 32 in the first direction D1 may be disposed at positions near the first guide rail 31, the second motor 112 configured to move the moving carriage 40 in the second direction D2 may be disposed at a position near the second guide rail 32, and the third motor 113 configured to increase or decrease the length of the post frame 50 in the third direction D3 may be disposed inside the moving carriage 40. In addition, the fourth motor 114 configured to rotate the photographic unit 70 in the fourth direction D4 may be disposed at a position near the first rotating joint 61, and the fifth motor 115 configured to rotate the photographic unit 70 in the fifth direction D5 may be disposed at a position near the second rotating joint 62.

Each motor of the motor unit 110 may be connected to a power transmission unit (not shown) to translate or rotate the photographic unit 70 in the first to fifth directions D1 to D5. The power transmission unit (not shown) may include a belt, a pulley, a chain, a sprocket, or any other element that is generally used as a power transmission unit.

The manipulating unit 80 is provided at one side of the photographic unit 70 to provide an interface through which various information related to X-ray imaging is input and each part of the radiographic apparatus is manipulated.

Referring to FIG. 4, the manipulating unit 80 includes a display unit 81 to provide an interface through which information related to X-ray imaging is input and each part of the radiographic apparatus is manipulated, and a grip 82 configured to be gripped by an operator to manually manipulate the radiographic apparatus. In addition, a button unit 84 is provided on the manipulating unit 80, and collision sensors 87 may be provided on the manipulating unit 80 as shown in FIG. 11. The illustration in FIG. 11 is merely an example of the collision sensors 87, and the position of the collision sensors 87 are not limited to the positions shown in FIG. 11. Also, additional collision sensors 87 may be provided at other locations on the manipulating unit 80. In one example, the collision sensors 87 are optical sensors configured to sense an object in a moving direction of the photographic unit 70 and output a signal corresponding to a distance to the sensed object. The system control unit 41 is configured to control the motors 111, 112, and 113 to prevent the photographic unit 70 from colliding with the sensed object based on the signal output from the collision sensors 87.

The button unit 84 includes a fourth direction rotation selecting button 85 and a fifth direction rotation selecting button 86 to be pressed by the operator when the operator desires to rotate the photographic unit 70 in the fourth direction or the fifth direction. That is, when the operator desires to rotate the photographic unit 70 in the fourth direction D4, the operator may rotate the photographic unit 70 after pressing the fourth direction rotation selecting button 85, or may rotate the photographic unit 70 while pressing the fourth direction rotation selecting button 85. When the operator desires to rotate the photographic unit 70 in the fifth direction D5, the operator may rotate the photographic unit 70 after pressing the fifth direction rotation selecting button 86, or may rotate the photographic unit 70 while pressing the fifth direction rotation selecting button 86. The illustration of the rotation selecting buttons 85 and 86 in FIG. 4 is merely an example, and the positions of the rotation selecting buttons 85 and 86 are not limited to the positions shown in FIG. 4.

Although the grip 82 is illustrated in FIG. 4 as being provided at a lower side of the manipulating unit 80, the position of the grip 82 is not limited to that position, and the grip 82 may be provided at a different position on the manipulating unit 80.

An operator may move and rotate the photographic unit 70 by gripping the grip 82 of the manipulating unit 80 to apply a force or a torque to the photographic unit 70. The movement and rotation of the photographic unit 70 in response to the force or torque applied by the operator will be described later.

The system control unit 41 is provided to control the devices provided in the radiographic apparatus, including the motor driver 100 and the manipulating unit 80, and is electrically connected to the devices provided in the radiographic apparatus. The system control unit 41 may be mounted inside the moving carriage 40.

The system control unit 41 is electrically connected to the motor driver 100 configured to drive each motor of the motor unit 110 to move the photographic unit 70 to a desired position.

For example, if the operator inputs a desired photographic position of the photographic unit 70 through the manipulating unit 80, the system control unit 41 determines a current position of the photographic unit 70 and the desired photographic position, and generates a control signal to control the operation of the motor unit 110 to move the photographic unit 70 to the desired photographic position, and outputs the generated control signal to the motor driver 100. The photographic unit 70 is moved to the desired photographic position by the operation of the motor 110. This mode of operation is referred to as an automatic movement mode. The automatic movement mode may be manipulated in a remote scheme through a remote controller including an interface that receives a command to move the photographic unit 70 to a desired position, or may be manipulated through the button unit 84 of the manipulating unit 80. Alternatively, the automatic movement mode may be manipulated through a workstation.

In addition, the operator may move the photographic unit 70 to a desired photographic position by directly applying a force or a torque to the photographic unit 70. This mode of operation is referred to as a manual movement mode. In order to convert from the automatic movement mode to the manual movement mode, a mode conversion unit 83 is provided. The mode conversion unit 83 may be mounted on the grip 82 of the manipulating unit 80 in the form of a switch. Alternatively, the mode conversion unit 83 may be integrally formed with the grip 82. The operation mode is converted to the manual movement mode if the operator grips the grip 82, and is converted to the automatic movement mode if the operator releases the grip 82. Alternatively, the operation mode may be converted to the manual movement mode without using the grip 82 if a force or a torque is detected by the measurement unit 126.

In the manual movement mode, a large force or a large torque must be applied to move the position of the photographic unit 70 since the frictional force generated by the motor unit 110 needs to be overcome. However, when the operator applies a force or a torque to the photographic unit 70, if the intention of the operator is recognized and the motor unit 110 is driven in response to the intention of the operator, the photographic unit 70 may be moved with a smaller force or torque than if the operator had to move the photographic unit 70 without the assistance of the motor unit 110. The manual movement mode in which the motor unit 110 is driven in response to the intention of the operator to move the photographic unit 70 may be referred to as a power-assisted movement mode to avoid confusion with a manual movement mode in which the user manually moves a photographic unit without a motor unit being driven.

Accordingly, in order to recognize the intention of the operator, the radiographic apparatus is provided with the measurement unit 126 to measure the force or the torque being applied to the photographic unit 70 by the operator. A signal indicating the force or torque measured by the measurement unit 126 is transmitted to the system control unit 41, and the system control unit 41 operates the motor unit 110 in response to the force or the torque measured by the measurement unit 126. The measurement unit 126 may include a force/torque sensor, and hereinafter will be referred to interchangeably as a measurement unit 126 or a force/torque sensor 126.

Figure 5:
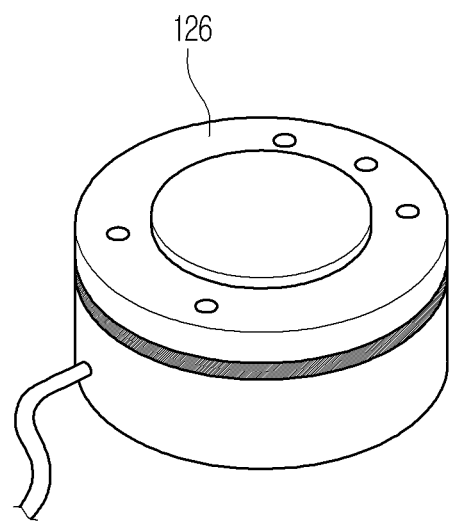
FIG. 5 is a perspective view illustrating a force/torque sensor of the radiographic apparatus of FIGS. 1-3 in accordance with one example.
Figure 6:
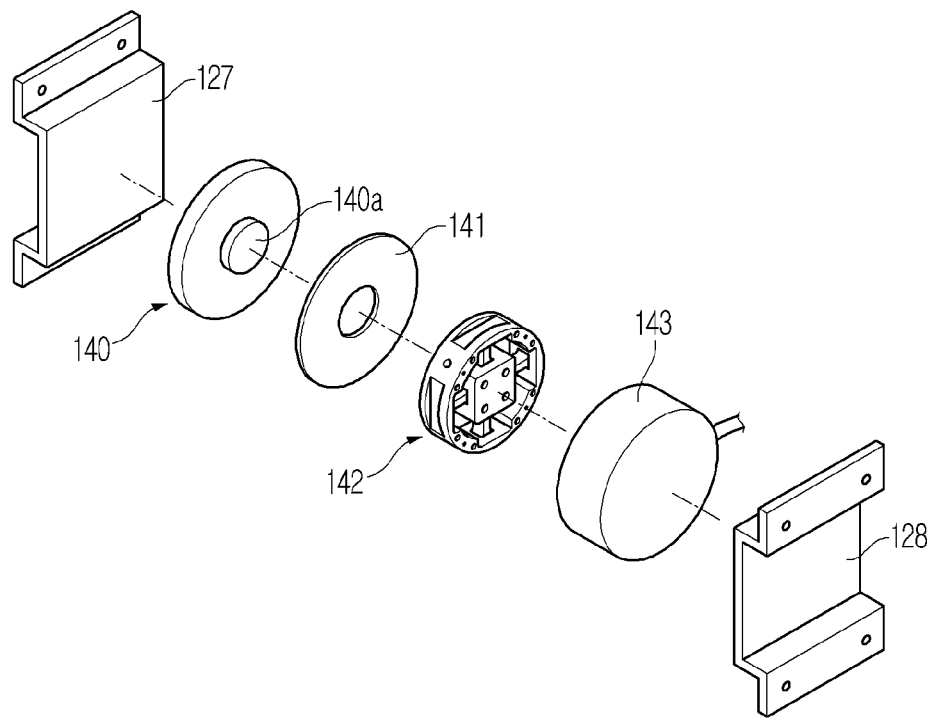
FIG. 6 is an exploded perspective view illustrating the force/torque sensor of FIG. 5 and brackets for mounting the force/torque sensor of FIG. 5 in accordance with one example.
Figure 7:
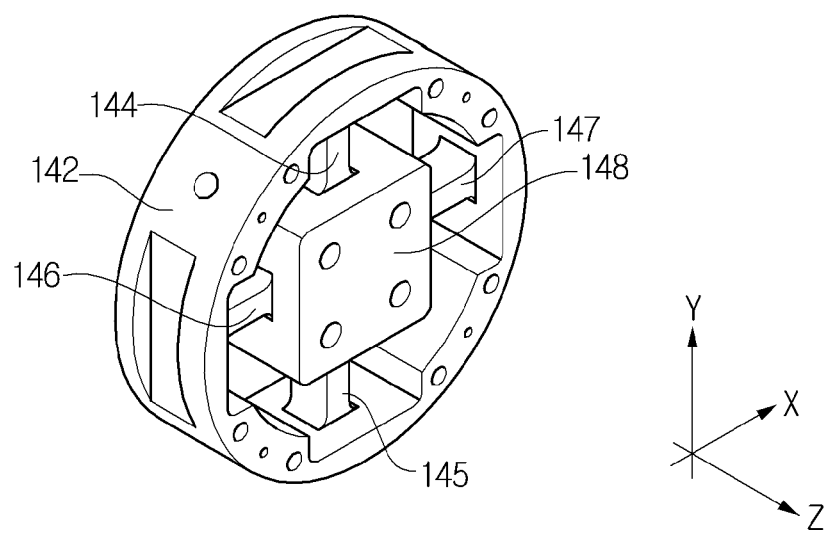
FIG. 7 is a perspective view illustrating a cross-shaped beam structure inside the force/torque sensor of FIGS. 5 and 6 in accordance with one example.
Figure 8:
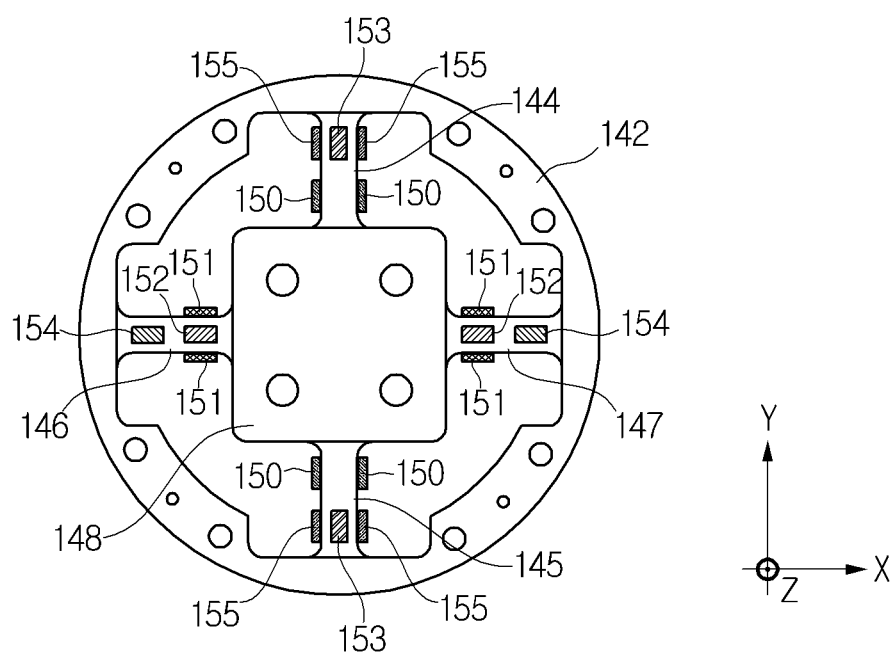
FIG. 8 is a front view illustrating the positions of strain gauges mounted on the cross-shaped beam structure of FIG. 7 in accordance with one example.
Figure 9:
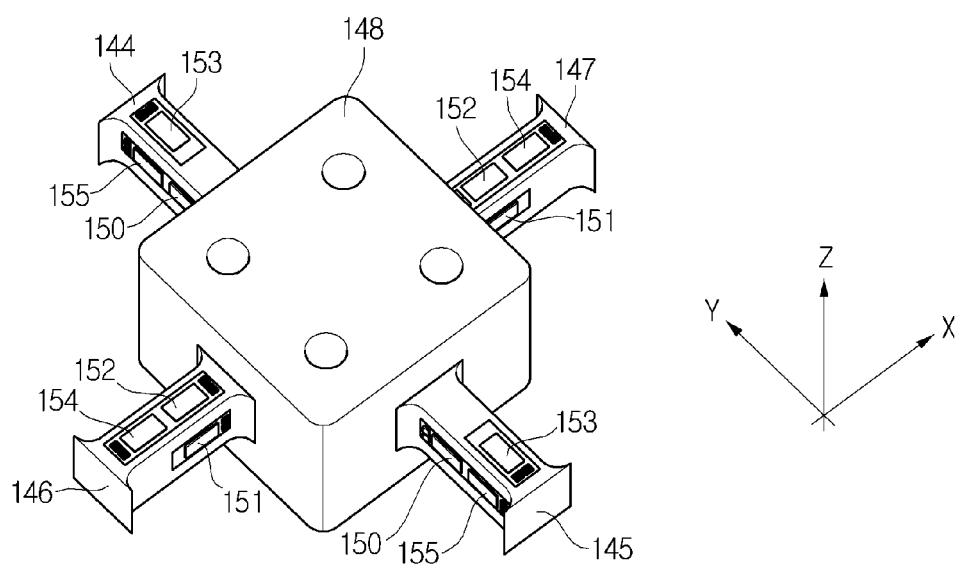
FIG. 9 is a perspective view illustrating the positions of the strain gauges mounted on the cross-shaped beam structure of FIG. 7 in accordance with one example.

FIG. 5 is a perspective view illustrating a force/torque sensor 126 of the radiographic apparatus of FIGS. 1-3 in accordance with one example. FIG. 6 is an exploded perspective view illustrating the force/torque sensor 126 of FIG. 5 and brackets 127 and 128 for mounting the force/torque sensor 126 of FIG. 5 in accordance with one example. FIG. 7 is a perspective view illustrating a cross-shaped beam structure inside the force/torque sensor 126 of FIGS. 5 and 6 in accordance with one example. FIG. 8 is a front view illustrating the positions of strain gauges 150 to 155 mounted on the force/torque sensor 126 in accordance with one example. FIG. 9 is a perspective view illustrating the positions of the strain gauges 150 to 155 mounted on the cross-shaped beam structure of FIG. 7 in accordance with one example. FIG. 10 is a block diagram illustrating the force/torque sensor 126 of FIGS. 5-9 in accordance with one example.

Although the measurement unit 126 in this example is implemented with the force/torque sensor 126, the measurement unit 126 is not limited thereto, and the measurement unit 126 may be implemented with various types of sensors capable of measuring a force acting on the photographic unit 70, such as a three-axis force sensor.

The force/torque sensor 126 may measure forces in three directions intersecting with one another, and torques having the three directions as rotation axes.

Since the force/torque sensor 126 is able to measure a total of three forces in three directions and a total of three torques having the three directions as rotation axes, the force/torque sensor 126 is able to measure forces in the first direction D1 to the third direction D3 of movement of the photographic unit 70 and torques in the fourth direction D4 and the fifth direction D5 of the movement of the photographic unit 70.

Although the measurement unit 126 may be implemented with the force/torque sensor 126 to measure the forces in the three directions intersecting one another and the torques having the three directions as rotation axes, the measurement unit 126 is not limited thereto. Since the directions requiring a larger force of an operator in moving the photographic unit 70 are the three directions intersecting one another, the measurement unit 126 may be implemented with a three-axis sensor configured to measure forces acting in at least three directions to assist the movement of the photographic unit 70.

Referring to FIG. 6, when the force/torque sensor 126 is mounted between the manipulating unit 80 and the photographic unit 70, a front surface member 140 of the force/torque sensor 126 is connected to a first bracket 127 configured to fix the force/torque sensor 126 to the manipulating unit 80, and a rear surface member 143 containing a cross-shaped beam structure 142 is connected to a second bracket 128 configured to fix the force/torque sensor 126 to the photographic unit 70. Although the first bracket 127 and the second bracket 128 are used to mount the force/torque sensor 126 between the manipulating unit 80 and the photographic unit 70 in this example, the method of mounting is not limited thereto, and the force/torque sensor 126 may be mounted between the manipulating unit 80 and the photographic unit 70 by use of a different mounting member or members. The front surface member 140 is separated from the rear surface member 143 by a connection member 141. The connection member 141 is not fastened to both the front surface member and the rear surface member, which enables the front surface member 140 to rotate relative to the rear surface member 143 when a torque is applied to the force/torque sensor 126. However, the connection member 141 may be omitted from the force/torque sensor 126.

The front surface member 140 has the form of the letter 'T' when viewed from the side, and is inserted into the rear surface member 143 through the connection member 141 to assemble the force/torque sensor 126. An insertion part 140a of the front surface member 140 corresponding to the stem of the letter 'T' is inserted into the rear surface member 143 through the connection member 141 and is fastened to a central portion 148 of the cross-shaped beam structure 142 mounted inside the rear surface member 143 to transmit the force or the torque applied to the manipulating unit 80 to the cross-shaped beam structure 142.

Since the insertion part 140a of the front surface member 140 is fastened to the central portion 148 of the cross-shaped beam structure 142, the central portion 148 of the cross-shaped beam structure 142 rotates with the front surface member 140 when a torque is applied to the force/torque sensor 126. Also, the outer rim of the cross-shaped beam structure 142 is fastened to the rear surface member 143 to prevent the outer rim of the cross-shaped beam structure 142 from rotating when a torque is applied to the force/torque sensor. This enables the central portion 148 of the cross-shaped beam structure 142 to rotate relative to the outer rim of the cross-shaped beam structure 142 when a torque is applied to the force/torque sensor 126.

A strain occurs in the cross-shaped beam structure 142 due to the force or torque transmitted through the front surface member 140, and this strain is measured by the strain gauges 150 to 155 mounted on the cross-shaped beam structure 142 as a change in resistance of the strain gauges 150 to 155. Although the cross-shaped beam structure 142 is used to measure the force or torque in this example, the force/torque sensor 126 is not limited to the cross-shaped beam structure 142, and a different structure may be used to measure the force or torque.

Referring to FIG. 7, the cross-shaped beam structure 142 is illustrated as being provided inside the rear surface member 143 of the force/torque sensor 126. The cross-shaped beam structure 142 will undergo a bending deformation corresponding to the force or torque applied from the outside. The strain gauges 150 to 155 are provided on surfaces of beams 144, 145, 146, and 147 as shown in FIGS. 8 and 9, and a resistance of each of the strain gauges 150 to 155 changes in proportion to the bending of the beam.

In order to measure the forces acting in the directions of the three axes intersecting one another, that is, the X axis, the Y-axis, and the Z-axis, four strain gauges 150 are provided the X-axis, four strain gauges 151 are provided for the Y-axis, and four strain gauges 152 are provided for the Z-axis.

For example, referring to FIGS. 8 and 9, in order to measure the force acting in the direction of the X-axis, four strain gauges 150 are provided on each lateral side of each of two beams 144 and 145 that are parallel to the Y-axis in the cross-shaped beam structure 142. In order to measure the force acting in the direction of the Y-axis, four strain gauges 151 are provided on each lateral side of each of two beams 146 and 147 that are parallel to the X-axis in the cross-shaped beam structure 142. In order to measure the force acting in the direction of the Z-axis, four strain gauges 152 are provided on a front and a rear of each of the two beams 146 and 147 that are parallel to the X-axis in the cross-shaped beam structure 142. In FIG. 8, the Z-axis is perpendicular to the plane of FIG. 8, and extends out of the plane of FIG. 8 as indicated by the dot in the circle at the intersection of the X-axis and the Y-axis.

In order to measure the torque having the X-axis as a rotation axis, four strain gauges 153 are provided on a front and a rear of each of the two beams 144 and 145 that are parallel to the Y-axis in the cross-shaped beam structure 142. In order to measure the torque having the Y-axis as a rotation axis, four strain gauges 154 are provided on a front and a rear of each of the two beams 146 and 147 that are parallel to the X-axis in the cross-shaped beam structure 142. In order to measure the torque having the Z-axis as a rotation axis, four strain gauges 155 are provided on each lateral side of each of the two beams 144 and 145 that are parallel to the Y-axis in the cross-shaped beam structure 142.

The installation positions and the number of the strain gauges 150 to 155 may be determined by the number of forces and torques to be measured, and are not limited to the positions and number described above.

The strain gauges 150 to 155 are connected in a bridge circuit. The bridge circuit may be implemented as a quarter bridge including a single strain gauge, a half bridge including two strain gauges, and a full bridge including four strain gauges. The bridge circuit in this example is implemented as a full bridge.

The full bridge is not easily affected by the temperature, and produces a small noise, and thus is suitable for a case where a high precision is required or a noise has a significant influence. In addition, the full bridge has a great ratio of output voltage to input voltage, and thus is suitable for the bridge circuit from the viewpoint of sensitivity.

In order to measure the forces acting in the three directions intersecting one another and the torques having the three directions as rotation axes as described above, a total of six sets of four strain gauges are provided, and a total of six full bridges are provided. That is, the four strain gauges 150 form a first set of four strain gauges and are connected in a first full bridge. The four strain gauges 151 form a second set of four strain gauges and are connected in a second full bridge. The four strain gauges 152 form a third set of four strain gauges and are connected in a third full bridge. The four strain gauges 153 form a fourth set of four strain gauges and are connected in a fourth full bridge. The four strain gauges 154 form a fifth set of four strain gauges and are connected in a fifth full bridge. The four strain gauges 155 form a sixth set of four strain gauges and are connected in a sixth full bridge.

The description of the force/torque sensor and the internal structure provided above is merely an example, and the measurement unit 126 is not limited thereto, and a different type of force/torque sensor having a different internal structure may be used.

The strain gauges used in the force/torque sensor 126 in this example may be a dual strain gauge having two strain gauges or a single strain gauge having only one strain gauge. In the following description, the reference number '150' will be used as a representative reference number of the strain gauge, but the description also applies to the strain gauges 151, 152, 153, 154, and 155.

A change in the resistance of the strain gauge 150 is converted to a voltage signal of microvolts or millivolts. As shown in FIG. 10, the voltage signal is amplified by an amplification unit 130 of the force/torque sensor 126. The amplified voltage signal is converted to a digital signal by an A/D converter (ADC) 132 included in a sensor control unit 131 of the force/torque sensor 126.

A firmware 133 of the sensor control unit 131 of the force/torque sensor 126 converts the digital signal to numerical data, and calculates effective data by performing a noise filtering operation and a calibration operation.

The firmware 133 converts the calculated data to adapt to a RS-232 communication protocol format that is defined between the system control unit 41 and the force/torque sensor 126 for transmission to the system control unit 41. The calculated data converted to adapt to the RS-232 communication protocol is converted to an electrical signal that conforms with the RS-232 standard by a Universal Synchronous/Asynchronous Receiver/Transmitter (USART) 134, and is transmitted to the system control unit 41.

Analog signals, such as the force or the torque applied to the force/torque sensor 126, are converted to digital signals by the force/torque sensor 126, and are transmitted to the system control unit 41.

As described above, information related to the direction and the magnitude of a force or a torque measured by the force/torque sensor 126 is transmitted to the system control unit 41, and is used by the system control unit 41 to generate a control signal to control the operation of the motor unit 110.

The force/torque sensor 126 is disposed at a position near the photographic unit 70 to recognize the intention of the operator by measuring the force or torque applied to the photographic unit 70 by the operator.

For example, the force/torque sensor 126 is disposed between the manipulating unit 80 and the photographic unit 70 as shown in FIG. 3. In the manual movement mode, the operator grips the grips 82 and applies a force or a torque to the grip 82, so the force/torque sensor 126 is disposed between the manipulating unit 80 and the photographic unit 70 as shown in FIG. 3.

As shown in FIG. 3, the force/torque sensor 126 is mounted between the manipulating unit 80 and the photographic unit 70 by the first bracket 127 disposed between the force/torque sensor 126 and the manipulating unit 80, and the second bracket 128 disposed between the force/torque sensor 126 and the photographic unit 70. In FIG. 11, the force/torque sensor 126 is illustrated as being mounted between the manipulating unit 80 and the photographic unit 70 by the first bracket 127 and the second bracket 128.

Since the force/torque sensor 126 is disposed between the manipulating unit 80 and the photographic unit 70, the force or torque applied to the grip 82 of the manipulating unit 80 by the operator may be precisely measured by the force torque sensor 126.

Alternatively, the force/torque sensor 126 may be mounted between the photographic unit 70 and the rotating joint unit 60, and may be connected to each of the photographic unit 70 and the rotating joint unit 60. If the force/torque sensor 126 is disposed in this manner, if the operator applies a force or torque to the photographic unit 70 without using the grip 82, the force or torque may still be precisely measured by the force/torque sensor 126.

Signals generated by the force/torque sensor 126, the collision sensor 74 mounted on the photographic unit 70, the collision sensors 87 mounted on the manipulating unit 80, and the manipulating unit 80 are transmitted to the system control unit 41 via a link board 73. That is, the link board 73 serves to relay the signals from the force/torque sensor 126, the collision sensors 74 and 87, and the manipulating unit 80 to the system control unit 41. Accordingly, the link board 73 is integrated with signal lines configured to deliver signals from the force/torque sensor 126, the collision sensors and 74 and 87, and the manipulating unit 80 to the link board 73. In addition, the link board 73 may include an A/D converter to convert analog signals to digital signals, so that in a case where analog signals are included in the signals transmitted to the link board 73 from the force/torque sensor 126, the collision sensors 74 and 87, and the manipulating unit 80, the A/D converter of the link board 73 converts the received analog signal to digital signals, thereby transmitting all signals in the form of a digital signal to the system control unit 41. As described above, the link board 73 serves to relay signals from the force/torque sensor 126, the collision sensors 74 and 87, and the manipulating unit 80 to the system control unit 41, and also serves to convert any analog signals to digital signals using the A/D converter included in the link board 73.

The link board 73 is installed inside the photographic unit 70 at the position shown in FIGS. 11 and 12.

The signals transmitted to the system control unit 41 via the link board 73 are transmitted through a RS-232 communication cable connected to the link board 73. The RS-232 communication cable extends through a corrugated tube 75 capable of expanding and contracting, and is connected to the system control unit 41.

Referring to FIGS. 11 and 12, since the corrugated tube 75 is connected to an opening 76 provided at an upper surface of the photographic unit 70, the link board 73 may be installed at a position adjacent to the opening 76 to which the corrugated tube 75 is connected so that the RS-232 communication cable easily extends through the corrugated tube 75.

The opening 76 to which the corrugated tube 75 is connected may be provided at a position that does not interfere with a region of the X-ray tube 71 configured to generate X-rays. Referring to FIG. 9, the opening 76 is provided at a region of the upper surface of the photographic unit 70 that is adjacent to a rear surface of the photographic unit 70 opposite to a front surface of the photographic unit 70 on which the manipulating unit 80 is installed. The link board 73 is installed at a lower side of the opening 76.

The corrugated tube 75 may be installed at a different position as long as it does not interfere with the region of the X-ray tube 71 configured to generate X-rays, and the link board 73 may be installed at a position adjacent to the corrugated tube 75 installed at the different position.

Since digital signals generated from the measurement results of the force/torque sensor 126 are transmitted to the system control unit 41 via the link board 73, the system control unit 41 receives information related to the force or the torque applied to the photographic unit 70 measured by the force/torque sensor 126, and generates a control signal to drive the motor unit 110 based on the received information.

In order to assist a translation movement of the photographic unit 70, the system control unit 41, based on a result of measurement of the force/torque sensor 126, determines a motor of the motors 111, 112, and 113 of the motor unit 110 that is configured to move the photographic unit 70 in a direction corresponding to a result of measurement of forces in three directions intersecting one another, and then generates a control signal to control the operation of the determined motor of the motor unit 110. In one example, the system control unit 41 is capable of generating control signals to control two or more of the motors 111, 112, and 113 simultaneously to move the photographic unit 70 (X-ray source unit) in two or more of the directions D1, D2, and D3 simultaneously if forces in two or more of the three directions intersecting one another (X-axis force, Y-axis force, and Z-axis force) are simultaneously sensed by the measurement unit 126 (sensor unit).

In order to generate the control signal to assist a translation movement of the photographic unit 70, the system control unit 41 uses information on forces acting in three directions intersecting one another.

When the photographic unit 70 is not moving, the motor unit 110 is coupled to a moving roller in a stopped state. Accordingly, if the photographic unit 70 is manually moved to a desired position, a clutch is required to disengage the motor unit 110 from the moving roller. In addition, in order to stop moving the photographic unit 70, a brake is required. The need to install the clutch and the brake during the manufacturing process of the radiographic apparatus complicates the manufacturing process.

However, in this example, the force applied to the photographic unit 70 is measured and the motor unit 110 is driven in response to the measured force to assist the movement of the photographic unit 70 in a direction in which the force is applied, thereby eliminating the need for the clutch and the brake that would otherwise be required to manually move the photographic unit 70. Accordingly, three clutches and three brakes required for translations in the three directions D1, D2, and D3 may be omitted in this example.

In order to assist a rotation movement of the photographic unit 70, the system control unit 41, based on a result of measurement of the force/torque sensor 126, determines a motor of the motors 114 and 115 of the motor unit 110 that is configured to rotate the photographic unit 70 in a direction corresponding to a result of measurement of a torque having one of the intersecting three directions as a rotation axis, and generates a control signal to control the operation of the determined motor of the motor unit 110.

In order to generate a control signal to assist a rotation movement of the photographic unit 70, the system control unit 41 uses information on at least one torque having at least one of the three directions as a rotation axis. In this example, the directions in which the photographic unit 70 are the directions D4 and D5, and accordingly the force/torque sensor 126 measures torques acting in the directions D4 and D5.

When the photographic unit 70 is not rotating, the motor unit 110 is coupled to a moving roller in a stopped state. Accordingly, if the photographic unit 70 is manually rotated to a desired position, a clutch is required to disengage the motor unit 110 from the moving roller. In addition, in order to stop rotating the photographic unit 70, a brake is required. The need to install the clutch and the brake during the manufacturing process of the radiographic apparatus complicates the manufacturing process.

However, in this example, the torque applied to the photographic unit 70 is measured and the motor unit 110 is driven in response to the measured torque to assist the rotation of the photographic unit 70 in a direction in which the torque is applied, thereby eliminating the need for the clutch and brake that would otherwise be required to manually rotate the photographic unit 70. Accordingly, two clutches and two brakes required for rotation in the directions D4 and D5 may be omitted in this example.

As a result, in this example, the force or torque applied to the photographic unit 70 is measured, and the motor unit 110 is driven in response to the measured force or torque to assist the movement or rotation of the photographic unit 70 in the direction in which the force or torque is applied, thereby eliminating the need for five clutches and five brakes that would otherwise be required to manually move or rotate the photographic unit 70.

Alternatively, if a smaller force is required to rotate the photographic unit 70 compared to a force required to translate the photographic unit 70, the radiographic apparatus may assist only the translation of the photographic unit 70 without assisting the rotation of the photographic unit 70. In this case, two clutches and two brakes that may be omitted when the rotation of the photographic unit 70 is assisted need to be installed.

If the translation and the rotation of the photographic unit 70 are not assisted, in order to translate and rotate the photographic unit 70, a larger force is required. To this end, the manipulating unit 80 is provided at both sides of the photographic unit with two grips that are gripped by both hands.

However, in this example, when the translation and the rotation of the photographic unit 70 are assisted in the manual movement mode, the photographic unit 70 may be translated or rotated with a smaller force, so the grip 82 of the manipulating unit 80 is provided in a form that is gripped by one hand. Accordingly, the space required for the grip 82 is reduced in the manipulating unit 80, enabling the display unit 81 to be larger. The enlarged display unit 81 enables the operator to check more information at once without an additional manipulation of the manipulating unit 80, thereby reducing the time taken for manipulation of the radiographic apparatus.

Hereinafter, a process of generating a control signal to assist a translation and a rotation of the photographic unit 70 based on the result of the measurement of the measurement unit 126 in the system control unit 41 will be described in detail with reference to FIG. 13.

Figure 13:
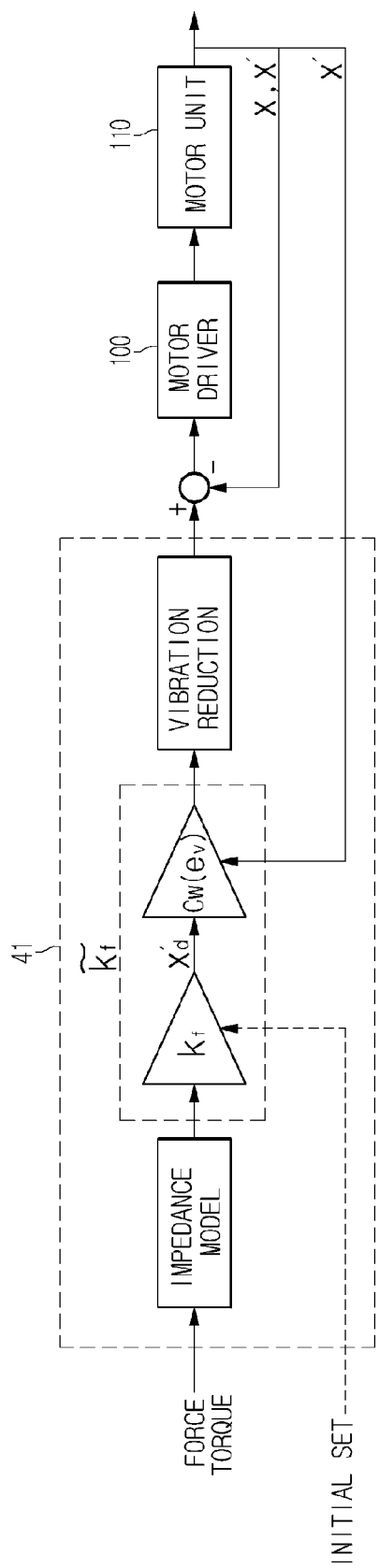
FIG. 13 is a control block diagram illustrating a process of generating a control signal to control a motor in a system control unit of the radiographic apparatus of FIGS. 1-12 in accordance with one example.

FIG. 13 is a control block diagram illustrating a process of generating a control signal to control a motor in a system control unit of the radiographic apparatus of FIGS. 1-12 in accordance with one example.

After the measurement unit 126 measures a force or a torque that are applied to the photographic unit 70, the system control unit 41 determines a motor of the motor unit 110 to provide a driving force in a direction of the force or the torque measured by the measurement unit 126.

For example, if the operator applies a force to the photographic unit 70 to move the photographic unit 70 in the first direction D1 while gripping the grip 82, the measurement unit 126 measures the force and transmits the measured force to the system control unit 41, and the system control unit 41 determines the first motors 111 that are configured to move the photographic unit 70 in the direction of the measured force transmitted from the measurement unit 126, that is, in the first direction D1, as a subject for control.

Similarly, if the operator applies a torque to the photographic unit 70 to rotate the photographic unit 70 in the fourth direction D4 while gripping the grip 82, the measurement unit 126 measures the torque and transmits the measured torque to the system control unit 41, and the system control unit 41 determines the fourth motor 114 that is configured to rotate the photographic unit 70 in a direction of the measured torque transmitted from the measurement unit 126, that is, in the fourth direction D4, as a subject of control.

After the motor of the motor unit 110 capable of providing a driving force in the direction of the force or the torque measured by the measurement unit 126 is determined based on the force or the torque measured by the measurement unit 126, the system control unit 41 determines a driving speed of the determined motor of the motor unit 110 based on the magnitude of the force or the torque measured by the measurement unit 126.

Referring to FIG. 13, the system control unit 41 calculates a control signal including a driving speed of $x_d'$ of the determined motor of the motor unit 110 corresponding to the force or the torque applied to the photographic unit 70 based on an impedance model. A transfer function G(S) between a force F(S) applied to the photographic unit 70 and a driving speed V(S) of the photographic unit 70 is defined by the following Equation 1.

$$G(S) = \frac{V(S)}{F(S)} = k_f \frac{\omega_n^2}{S^2 + 2\zeta\omega_n S + \omega_n^2} \quad (1)$$

In Equation 1, $k_f$ denotes a speed/force ratio coefficient, and may be set by the operator depending on the requirements of the operator. In order to achieve a precise movement of the photographic unit 70, $k_f$ may be set to be smaller than a predetermined value, and in order to achieve an easy movement of the photographic unit 70, $k_f$ may be set to be larger than the predetermined value. $\zeta$ denotes a damping factor that is set to be larger than 1 to prevent an overshoot that may cause an unexpected movement of the photographic unit 70, and $\omega_n$ denotes an undamped natural frequency that is determined depending on the driving condition of the apparatus.

Although the transfer function G(S) is provided in the form of a second-order low-pass filter as shown in Equation 1, the transfer function G(S) is not limited thereto, and may be provided in the form of a first-order filter, or in the form of a third- or higher-order filter.

In addition, in a case in which a larger force is abruptly applied to the apparatus, for example, in a case in which an operator collides with the apparatus, or a larger force is applied to the apparatus due to an erroneous operation of the apparatus, the system control unit 41 prevents oscillation caused by such an abrupt larger force.

The system control unit 41 calculates a weighted speed/force ratio coefficient $\tilde{k}_f$ having a weight function applied thereto in real time in order to prevent oscillation. The following Equation 2 defines the weighted speed/force ratio coefficient $\tilde{k}_f$.

$$\tilde{k}_f = C_w(e_v)k_f, \quad C_w(e_v) = 0.5\frac{e^{-a(|e_v|-b)} - 1}{e^{-a(|e_v|-b)} + 1} + 1 \quad (2)$$

In Equation 2, $C_w$ denotes a weight function, and $e_v$ denotes a speed error, that is, a difference between a driving speed $x_d'$ of the photographic unit 70 calculated through the impedance model and a speed x' at which the photographic unit 70 actually moves, $k_f$ denotes the speed/force ratio coefficient set by the operator, and a and b denote adjustment constants.

An abrupt increase or decrease of a force being applied to the photographic unit 70 results in a speed error, that is, results in $e_v$ increasing, and with the increase of $e_v$, the weight function $C_w(e_v)$ decreases, and thus the weighted speed/force ratio coefficient $\tilde{k}_f$ decreases. Accordingly, the system has a high damping coefficient, and as the moving speed of the photographic unit 70 decreases or the photographic unit 70 stops moving, oscillation does not occur.

The degree to which the weight function $C_w(e_v)$ decreases as $e_v$ increases varies depending on the adjustment constant a. If the adjustment constant a is larger, the weight function $C_w(e_v)$ decreases nonlinearly. The weight function $C_w(e_v)$ starts decreasing in a nonlinear manner if the speed error $e_v$ exceeds a predetermined value, and thus the moving speed x' of the photographic unit 70 decreases or the photographic unit 70 stops moving. A value of the speed error $e_v$ causing the weight function $C_w(e_v)$ to start decreasing may be set in advance depending on the value a and may be stored. Accordingly, if the speed error $e_v$ equals or exceeds the value of the speed error $e_v$ set in advance and stored, the system control unit 41 reduces the moving speed of the photographic unit 70 or stops moving the photographic unit 70.

After the system control unit 41 calculates the control signal including the driving speed $x_d'$ of the determined motor of the motor unit 110, the system control unit 41 removes a signal having a frequency range corresponding to a resonance frequency range of the radiographic apparatus from the control signal to reduce vibration generated when the photographic unit 70 moves.

A transfer function N(S) of a notch filter to remove a signal of a resonance frequency range is defined by the following Equation 3.

$$N(S) = \frac{S^2 + \omega_o^2}{S^2 + \frac{\omega_o}{Q}S + \omega_o^2} \quad (3)$$

In Equation 3, $\omega_o$ denotes a notch frequency that is a resonance frequency of the radiographic apparatus, and Q denotes a quality factor. A stop bandwidth that is removed by the notch filter is determined by a ratio of the notch frequency to the quality factor, that is, $\omega_o/Q$.

In FIG. 13, the blocks labeled "IMPEDANCE MODEL" and "$k_f$" together perform a calculation according to Equation 1 above; the block labeled "$C_w(e_v)$" performs a calculation according to Equation 2 above, and the block labeled "VIBRATION REDUCTION" performs a calculation according to Equation 3 above. The input labeled "INITIAL SET" enables the operator to set $k_f$ to a desired value.

One control circuit as shown in FIG. 13 is provided for each of the motors 111, 112, 113, 114, and 115 of the motor unit 110. However, only one control circuit may be provided for the two motors 111. The control circuit provided for the two motors 111 receives a force measured in the direction D1 by the measurement unit 126 as an input. The control circuit provided for the motor 112 receives a force measured in the direction D2 by the measurement unit 126 as an input. The control circuit provided for the motor 113 receives a force measured in the direction D3 by the measurement unit 126 as an input. The control circuit provided for the motor 114 receives a torque measured in the direction D4 as an input. The control circuit provided for the motor 115 received a torque measured in the direction D5 as an input. In an example in which the radiographic apparatus assists only the translation of the photographic unit 70 without assisting the rotation of the photographic unit 70 as described above, one control circuit as shown in FIG. 13 is provided for each of the motors 111, 112, and 113 of the motor unit 110. Again, only one control circuit may be provided for the two motors 111.

The system control unit 41 applies the notch filter to the calculated control signal, and converts the calculated control signal to which the notch filter has been applied to a form satisfying the CANopen (Controller Area Network open) communication profile DS-402, and transmits the converted control signal to the motor driver 100.

The communication between the system control unit 41 and the motor driver 100 in this example supports the CANopen communication profile DS-301, DS-305, DS-402 industrial standard profile based on a CAN communication interface. The communication between the system control unit 41 and the motor driver 100 may be achieved through a CAN communication cable.

The motor driver 100 generates a three-phase AC voltage signal to drive the determined motor of the motor unit 110 according to the control signal transmitted from the system control unit 41, and outputs the generated three-phase AC voltage signal to the determined motor of the motor unit 110. The determined motor of the motor unit 110, according to the voltage signal transmitted from the motor driver 100, assists the photographic unit 70 in the movement in the direction of the force or the torque measured by the measurement unit 126. Referring to FIG. 13, the motor unit 110 feeds back the driving speed x' and the moving distance x of the determined motor to the system control unit 41. The system control unit 41 updates the control signal in real time based on the feedback information, thereby performing a precise assistance.

Accordingly, when the photographic unit 70 is moved to a desired position with the assistance of the motor unit 110, the operator may move the photographic unit 70 with a smaller force or torque, thereby reducing the fatigue caused by the manual manipulation of the photographic unit 70.

As the photographic unit 70 is moved with the assistance of the motor unit 110, the system control unit 41 outputs an alarm sound indicating the movement of the photographic unit 70 from the sound output unit 42 shown in FIG. 1, thereby notifying the operator that the movement of the photographic unit 70 is achieved with the assistance of the motor unit 110.

Different types of alarm sounds corresponding to different movement modes of the photographic unit 70 may be stored in advance. For example, the alarm sounds may include an alarm sound indicating that the photographic unit 70 is being moved in the automatic movement mode, and an alarm sound indicating that the photographic unit 70 is being moved in the manual movement mode. Accordingly, the operator may recognize the current movement mode based on the type of alarm sound being output.

Other sounds to be output from the sound output unit 52 that are related to various motions of the radiographic apparatus as well as the movement of the photographic unit 70 may be stored in advance. For example, various types of a camera shutter sound may be stored in advance so that a camera shutter sound is output when radiography is performed by the radiographic apparatus. When radiography is performed, the camera shutter sound stored in advance may be output from the sound output unit 42.

Figure 14:
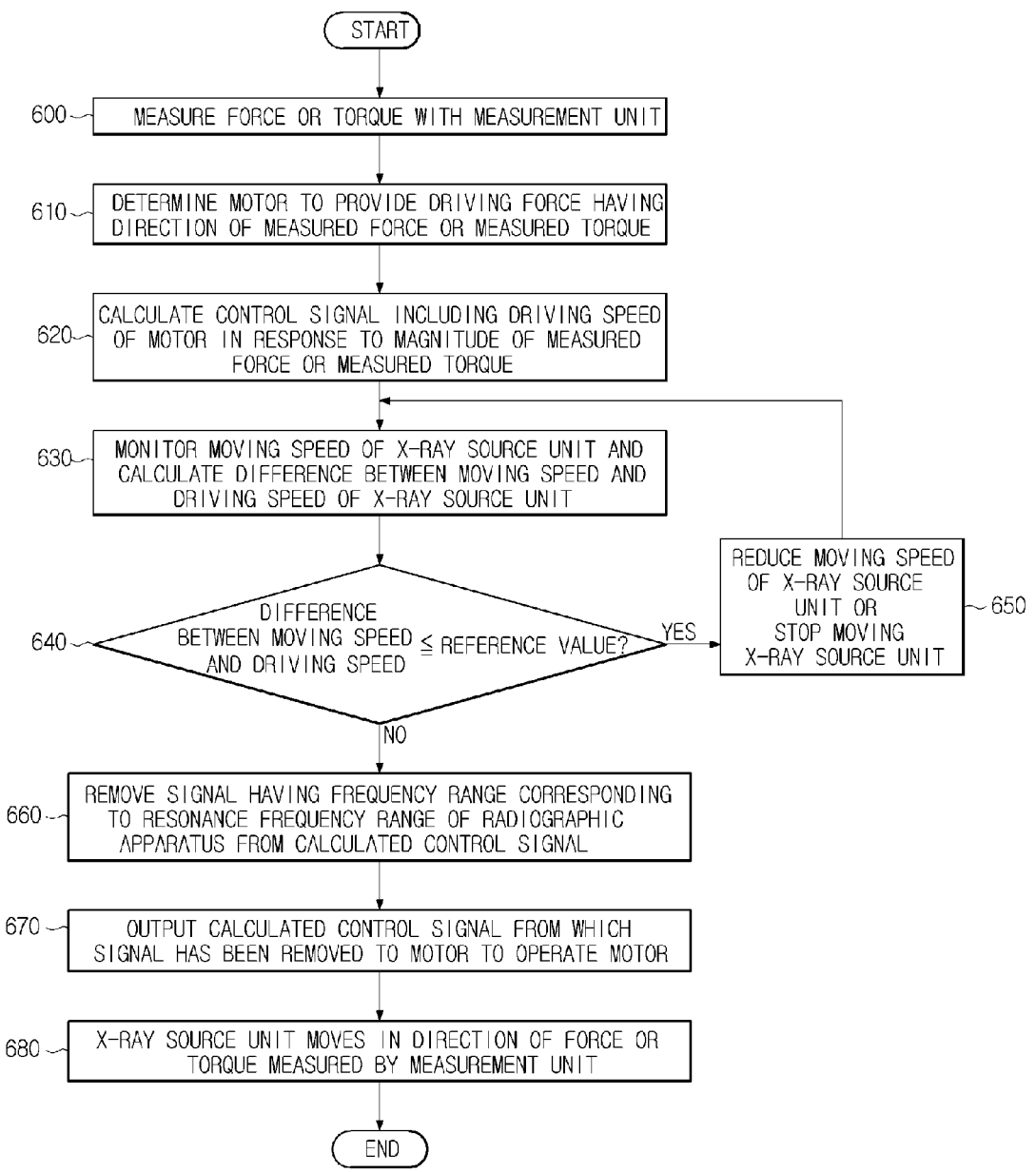
FIG. 14 is a flow chart illustrating a method of controlling the radiographic apparatus of FIGS. 1-13 in accordance with one example.

FIG. 14 is a flow chart illustrating a method of controlling the radiographic apparatus of FIGS. 1-13 in accordance with one example. Referring to FIG. 14, a force or a torque applied to the photographic unit 70 is measured by the measurement unit 126 (600) as described above in connection with FIGS. 1-13.

After the measurement unit 126 measures the force or the torque applied to the photographic unit 70, the system control unit 41 determines a motor of the motors 111, 112, 113, 114, and 115 of the motor unit 110 capable of providing a driving force in a direction of the measured force or the measured torque (610) as described above in connection with FIG. 13.

After the motor of the motor unit 110 is determined, the system control unit 41 calculates a control signal including a driving speed of the determined motor of the motor unit 110 based on the measured force or the measured torque (620) as described above in connection with FIG. 13. In one example, the system control unit 41 is capable of calculating control signals to control two or more of the motors 111, 112, and 113 simultaneously to move the photographic unit 70 (X-ray source unit) in two or more of the directions D1, D2, and D3 simultaneously if forces in two or more of the three directions intersecting one another (X-axis force, Y-axis force, and Z-axis force) are simultaneously sensed by the measurement unit 126 (sensor unit).

The system control unit 41 monitors a moving speed of the photographic unit 70, and calculates a difference between the moving speed of the photographic unit 70 and the driving speed of the photographic unit (630) as described above in connection with FIG. 13, determines whether the difference equals or exceeds a predetermined reference value (640) as described above in connection with FIG. 13, and reduces the moving speed of the photographic unit 70 or stops moving the photographic unit 70 if the difference equals or exceeds the predetermined reference value (650) as described above in connection with FIG. 13.

If the difference between the moving speed of the photographic unit 70 and the driving speed of the photographic unit 70 is smaller than the predetermined reference value, the control unit removes a signal having a frequency range corresponding to a resonance frequency range of the radiographic apparatus from the calculated control signal including the driving speed of the determined motor of the motor unit 110 (660) as described above in connection with FIG. 13.

The system control unit 41 outputs the calculated control signal from which the signal having the frequency range corresponding to the resonance frequency range of the radiography apparatus has been removed to the determined motor of the motor unit 110 to operate the determined motor of the motor unit 110 (670) as described above in connection with FIG. 13, and as the determined motor of the motor unit 110 operates according to the control signal of the system control unit 41, the photographic unit 70 moves in the direction of the force or the torque measured by the measurement unit 126 (680) as described above in connection with FIG. 13.

The system control unit 41, the manipulating unit 80, the motor driver 100, the measurement unit or force/torque sensor 126, the firmware 133, the USART 134, and the RS-232 driver 135 described above may be implemented using one or more hardware components, one or more software components, or a combination of one or more hardware components and one or more software components.

A hardware component may be, for example, a physical device that physically performs one or more operations, but is not limited thereto. Examples of hardware components include amplifiers, differential amplifiers, operational amplifiers, low-pass filters, high-pass filters, band-pass filters, analog-to-digital converters, digital-to-analog converters, registers, differentiators, comparators, arithmetic units, functional units, memory devices, radio cards, and processing devices.

A software component may be implemented, for example, by a processing device controlled by software or instructions to perform one or more operations, but is not limited thereto. A computer, controller, or other control device may cause the processing device to run the software or execute the instructions. One software component may be implemented by one processing device, or two or more software components may be implemented by one processing device, or one software component may be implemented by two or more processing devices, or two or more software components may be implemented by two or more processing devices.

A processing device may be implemented using one or more general-purpose or special-purpose computers, such as, for example, a processor, a controller and an arithmetic logic unit, a digital signal processor, a microcomputer, a field-programmable array, a programmable logic unit, a microprocessor, or any other device capable of running software or executing instructions. The processing device may run an operating system (OS), and may run one or more software applications that operate under the OS. The processing device may access, store, manipulate, process, and create data when running the software or executing the instructions. For simplicity, the singular term "processing device" may be used in the description, but one of ordinary skill in the art will appreciate that a processing device may include multiple processing elements and multiple types of processing elements. For example, a processing device may include one or more processors, or one or more processors and one or more controllers. In addition, different processing configurations are possible, such as parallel processors or multi-core processors.

A processing device configured to implement a software component to perform an operation A may include a processor programmed to run software or execute instructions to control the processor to perform operation A. In addition, a processing device configured to implement a software component to perform an operation A, an operation B, and an operation C may have various configurations, such as, for example, a processor configured to implement a software component to perform operations A, B, and C; a first processor configured to implement a software component to perform operation A, and a second processor configured to implement a software component to perform operations B and C; a first processor configured to implement a software component to perform operations A and B, and a second processor configured to implement a software component to perform operation C; a first processor configured to implement a software component to perform operation A, a second processor configured to implement a software component to perform operation B, and a third processor configured to implement a software component to perform operation C; a first processor configured to implement a software component to perform operations A, B, and C, and a second processor configured to implement a software component to perform operations A, B, and C, or any other configuration of one or more processors each implementing one or more of operations A, B, and C. Although these examples refer to three operations A, B, C, the number of operations that may implemented is not limited to three, but may be any number of operations required to achieve a desired result or perform a desired task.

Software or instructions for controlling a processing device to implement a software component may include a computer program, a piece of code, an instruction, or some combination thereof, for independently or collectively instructing or configuring the processing device to perform one or more desired operations. The software or instructions may include machine code that may be directly executed by the processing device, such as machine code produced by a compiler, and/or higher-level code that may be executed by the processing device using an interpreter. The software or instructions and any associated data, data files, and data structures may be embodied permanently or temporarily in any type of machine, component, physical or virtual equipment, computer storage medium or device, or a propagated signal wave capable of providing instructions or data to or being interpreted by the processing device. The software or instructions and any associated data, data files, and data structures also may be distributed over network-coupled computer systems so that the software or instructions and any associated data, data files, and data structures are stored and executed in a distributed fashion.

For example, the software or instructions and any associated data, data files, and data structures may be recorded, stored, or fixed in one or more non-transitory computer-readable storage media. A non-transitory computer-readable storage medium may be any data storage device that is capable of storing the software or instructions and any associated data, data files, and data structures so that they can be read by a computer system or processing device. Examples of a non-transitory computer-readable storage medium include read-only memory (ROM), random-access memory (RAM), flash memory, CD-ROMs, CD-Rs, CD+Rs, CD-RWs, CD+RWs, DVD-ROMs, DVD-Rs, DVD+Rs, DVD-RWs, DVD+RWs, DVD-RAMs, BD-ROMs, BD-Rs, BD-R LTHs, BD-REs, magnetic tapes, floppy disks, magneto-optical data storage devices, optical data storage devices, hard disks, solid-state disks, or any other non-transitory computer-readable storage medium known to one of ordinary skill in the art.

Functional programs, codes, and code segments for implementing the examples disclosed herein can be easily constructed by a programmer skilled in the art to which the examples pertain based on the drawings and their corresponding descriptions as provided herein.

While this disclosure includes specific examples, it will be apparent to one of ordinary skill in the art that various changes in form and details may be made in these examples without departing from the spirit and scope of the claims and their equivalents. The examples described herein are to be considered in a descriptive sense only, and not for purposes of limitation. Descriptions of features or aspects in each example are to be considered as being applicable to similar features or aspects in other examples. Suitable results may be achieved if the described techniques are performed in a different order, and/or if components in a described system, architecture, device, or circuit are combined in a different manner and/or replaced or supplemented by other components or their equivalents. Therefore, the scope of the disclosure is defined not by the detailed description, but by the claims and their equivalents, and all variations within the scope of the claims and their equivalents are to be construed as being included in the disclosure.

What is claimed is:
1. A radiographic apparatus comprising:
   an X-ray source unit;
   a measuring device configured to measure a force applied to the measuring device;
   a motor; and
   a control device configured to provide a power-assisted mode and an automated mode, the control device being configured to control the motor to move the X-ray source unit in the power-assisted mode based on a direction and a magnitude of the force measured by the measuring device, and, in response to a user inputting a desired position of the X-ray source unit, to control the motor used in the power-assisted mode to move the X-ray source unit in the automated mode based on the desired position of the X-ray source unit input by the user.
2. The radiographic apparatus of claim 1, further comprising a power transmission unit configured to move the X-ray source unit in response to a driving force applied to the power transmission unit by the motor;
   wherein the motor is constantly engaged with the power transmission unit regardless of whether the control device is operating in the power-assisted mode or the automated mode.

3. The radiographic apparatus of claim 1, wherein the motor is coupled to the X-ray source unit without any clutch configured to disengage the motor from the X-ray source unit.

4. The radiographic apparatus of claim 3, wherein the radiographic apparatus does not comprise any brake configured to brake the X-ray source unit in any of an x-axis direction, a y-axis direction, and a z-axis direction.

5. The radiographic apparatus of claim 1, further comprising an operating panel unit configured to input information for operating the radiographic apparatus;
   wherein the measuring device is mounted on the X-ray source unit; and
   the operating panel unit is mounted on the measuring device.

6. The radiographic apparatus of claim 1, wherein the control device is further configured to control the motor to move the X-ray source unit in the power-assisted mode based on the direction and the magnitude of the force measured by the measuring device and a control parameter having an initial value that is settable by the user.

7. The radiographic apparatus of claim 6, wherein the control parameter is a speed/force ratio coefficient.

8. The radiographic apparatus of claim 6, wherein the control device is further configured to:
   calculate a speed at which the X-ray source unit is to move in the power-assisted mode based on the direction and the magnitude of the force measured by the measuring device;
   control the motor to move the X-ray source unit in the power-assisted mode based on the calculated speed and the initial value of the control parameter;
   calculate a speed error between the calculated speed of the X-ray source unit and an actual speed of the X-ray source unit;
   apply a weight to the initial value of the control parameter according to a weight function that depends on the speed error to obtain a weighted control parameter; and
   control the motor to move the X-ray source unit in the power-assisted mode based on the calculated speed and the weighted control parameter.

9. The radiographic apparatus of claim 8, wherein the weight function decreases as the speed error increases.

10. The radiographic apparatus of claim 1, wherein the control device is further configured to:
   calculate a speed at which the X-ray source unit is to move in the power-assisted mode based on the direction and the magnitude of the force measured by the measuring device;
   control the motor to move the X-ray source unit in the power-assisted mode based on the calculated speed;
   calculate a speed error between the calculated speed of the X-ray source unit and an actual speed of the X-ray source unit; and
   control the motor to reduce a speed at which the X-ray source unit is moving, or to stop moving the X-ray source unit, in response to the speed error exceeding a predetermined speed error.

11. The radiographic apparatus of claim 1, wherein the control device is further configured to:
   generate a control signal for controlling the motor to move the X-ray source unit based on the direction and the magnitude of the force measured by the measuring device;
   remove a signal having a predetermined frequency range corresponding to a predetermined resonance frequency range of the radiographic apparatus from the control signal to reduce a vibration generated when the motor moves the X-ray source unit in response to the control signal; and
   control the motor to move the X-ray source unit in the power-assisted mode based on the control signal from which the signal having the predetermined frequency range has been removed.

12. The radiographic apparatus of claim 11, wherein the control unit comprises a notch filter having a predetermined notch frequency configured to remove the signal having the predetermined frequency range corresponding to the predetermined resonance frequency range of the radiographic apparatus from the control signal to reduce the vibration generated when the motor moves the X-ray source unit in response to the control signal.

13. The radiographic apparatus of claim 1, further comprising a collision sensor configured to sense an object in a moving direction of the X-ray source unit, and output a signal corresponding to a distance to the sensed object;
   wherein the control device is further configured to control the motor to prevent the X-ray source unit from colliding with the object based on the signal output from the collision sensor.

14. A radiographic apparatus comprising:
   an X-ray source unit;
   a measuring device configured to measure a force applied to the measuring device;
   a motor; and
   a control device configured to provide a power-assisted mode and an automated mode the control device being configured to control the motor to move the X-ray source unit in the power-assisted mode based on a direction and a magnitude of the force measured by the measuring device, and to control the motor used in the power-assisted mode to move the X-ray source unit in the automated mode based on a desired position of the X-ray source unit input by a user;
   wherein the control device is further configured to switch between the power-assisted mode and the automated mode in response to an instruction from the user.

15. A radiographic apparatus comprising:
   an X-ray source unit;
   a measuring device configured to measure a force applied to the measuring device;
   a motor;
   a control device configured to provide a power-assisted mode and an automated mode, the control device being configured to control the motor to move the X-ray source unit in the power-assisted mode based on a direction and a magnitude of the force measured by the measuring device, and to control the motor used in the power-assisted mode to move the X-ray source unit in the automated mode based on a desired position of the X-ray source unit input by a user; and
   a mode conversion switch configured to be actuated by the user;
   wherein the control device is further configured to switch from the automated mode to the power-assisted mode in response to the mode conversion switch being actuated by the user, and to switch from the power-assisted mode to the automated mode in response to the mode conversion switch being released by the user.

16. A radiographic apparatus comprising:
an X-ray source unit;
a measuring device configured to measure a force applied to the measuring device;
a motor; and
a control device configured to control the motor to move the X-ray source unit in a power-assisted mode in response to the force measured by the measuring device, and to control the motor used in the power-assisted mode to move the X-ray source unit in an automated mode initiated by a user.

17. The radiographic apparatus of claim 16, further comprising a power transmission unit configured to move the X-ray source unit in response to a driving force applied to the power transmission unit by the motor;
wherein the motor is constantly engaged with the power transmission unit regardless of whether the control device is operating in the power-assisted mode or the automated mode.

18. A control apparatus for a radiographic apparatus, the control apparatus comprising:
a measuring device configured to measure a force applied to the measuring device; and
a control device configured to control a motor of the radiographic apparatus to move an X-ray source unit of the radiographic apparatus in a power-assisted mode in response to the force measured by the measuring device, and to control the motor used in the power-assisted mode to move the X-ray source unit in an automated mode initiated by a user.

19. A radiographic apparatus comprising:
an X-ray source unit;
a measuring device configured to measure a force applied to the measuring device; and
a control device configured to provide a power-assisted mode and an automated mode, the control device being configured to control movement of the X-ray source unit in three directions in the power-assisted mode by controlling three motors based on the force measured by the measuring device, and, in response to a user inputting a desired position of the X-ray source unit, to control movement of the X-ray source unit in the three directions in the automated mode by controlling the three motors used in the power-assisted mode based on a the desired position of the X-ray source unit input by the user.

20. The radiographic apparatus of claim 19, further comprising three power transmission units each configured to move the X-ray source unit in response to a respective driving force applied to the power transmission unit by a respective one of the three motors;
wherein each of the three motors is constantly engaged with a respective one of the power transmission units regardless of whether the control device is operating in the automated mode or the power-assisted mode.

21. The radiographic apparatus of claim 19, further comprising an operating panel unit mounted on the measuring device and configured to input information for operating the radiographic apparatus; and
a grip mounted on the operating panel unit and configured to be gripped by the user to apply the force to the measuring device via the operating panel unit.

22. The radiographic apparatus of claim 21, wherein the measuring device is mounted on the X-ray source unit.

23. The radiographic apparatus of claim 19, wherein the three motors comprise:
a first motor configured to move the X-ray source unit in an x-axis direction;
a second motor configured to move the X-ray source unit in a y-axis direction; and
a third motor configured to move the X-ray source unit in a z-axis direction; and
the first motor, the second motor, and the third motor are coupled to the X-ray source unit without any clutches configured to disengage any of the first motor, the second motor, and the third motor from the X-ray source unit.

24. The radiographic apparatus of claim 23, wherein the radiographic apparatus does not comprise any brake configured to brake the X-ray source unit in any of the x-axis direction, the y-axis direction, and the z-axis direction.

25. The radiographic apparatus of claim 19, further comprising:
a first guide rail mounted on a ceiling and extending in an x-axis direction;
a second guide rail slidably mounted on the first rail and extending in a y-axis direction; and
a post frame slidably mounted on the second guide rail and configured to have a length that is increasable and decreasable in a z-axis direction;
wherein the X-ray source unit is supported by the post frame; and
the three motors comprise:
a first motor configured to move the second guide rail along the first guide rail in the x-axis direction to move the X-ray source unit in the x-axis direction;
a second motor configured to move the post frame along the second guide rail in the y-axis direction to move the X-ray source unit in the y-axis direction; and
a third motor configured to increase and decrease the length of the post frame in the z-axis direction to move the X-ray source unit in the z-axis direction.

26. The radiographic apparatus of claim 19, wherein the measuring device is configured to measure the force applied to the measurement device as three force components in the three directions; and
the control device is further configured to control the movement of the X-ray source unit in the three directions in the power-assisted mode by controlling the three motors based on the three force components in the three directions.

27. A radiographic apparatus comprising:
an X-ray source unit;
a measuring device configured to measure a force applied to the device; and
a control device configured to provide a power-assisted mode and an automated mode, the control device being configured to control movement of the X-ray source unit in three directions in the power-assisted mode by controlling three motors based on the force measured by the measuring device, and to control movement of the X-ray source unit in the three directions in the automated mode by controlling the three motors used in the power-assisted mode based on a desired position of the X-ray source unit input by a user;
wherein the control device is further configured to switch between the power-assisted mode and the automated mode in response to an instruction from the user.

28. A radiographic apparatus comprising:
an X-ray source unit;

a measuring device configured to measure a force applied to the measuring device;

a control device configured to provide a power-assisted mode and an automated mode, the control device being configured to control movement of the X-ray source unit in three directions in the power-assisted mode by controlling three motors based on the force measured by the measuring device, and to control movement of the X-ray source unit in the three directions in the automated mode by controlling the three motors used in the power-assisted mode based on a desired position of the X-ray source unit input by a user; and a mode conversion switch configured to be actuated by the user;

wherein the control device is further configured to switch from the automated mode to the power-assisted mode in response to the mode conversion switch being actuated by the user, and to switch from the power-assisted mode to the automated mode in response to the mode conversion switch being released by the user.

29. The radiographic apparatus of claim 28, further comprising an operating panel unit mounted on the measuring device and configured to input information for operating the radiographic apparatus; and a grip mounted on the operating panel unit and configured to be gripped by the user to apply the force to the measuring device via the operating panel unit;

wherein the mode conversion switch is mounted on the grip and is configured to be actuated by the user in response to the user gripping the grip to apply the force to the measuring device via the operating panel unit.

30. The radiographic apparatus of claim 29, wherein the measuring device is mounted on the X-ray source unit.

31. A radiographic apparatus comprising:

an X-ray source unit;

a sensing device configured to sense a direction of a force applied to the sensing device;

a motor; and a control device configured to provide a power-assisted mode and an automated mode, the control device being configured to control the motor to move the X-ray source unit in the power-assisted mode based on the direction of the force sensed by the sensing device, and, in response to a user inputting a desired position of the X-ray source unit, to control the motor used in the power-assisted mode to move the X-ray source unit in the automated mode based on the desired position of the X-ray source unit input by the user.

* * * * *